US012569613B2

(12) United States Patent     (10) Patent No.:   US 12,569,613 B2

DeSensi et al.     (45) Date of Patent:    Mar. 10, 2026

(54) SYSTEM, METHOD, AND COMPUTER PROGRAM PRODUCT FOR PROVIDING ACCESS TO FLUID INJECTION SYSTEMS

(71) Applicant: BAYER HEALTHCARE LLC, Whippany, NJ (US)

(72) Inventors: Frank DeSensi, Allison Park, PA (US); Barry Skirble, Allison Park, PA (US); Anthony Scolieri, Glenshaw, PA (US); Karthikeyan Ranganathan, Gibsonia, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 229 days.

(21) Appl. No.: 18/030,138

(22) PCT Filed: Oct. 4, 2021

(86) PCT No.: PCT/US2021/053359

§ 371 (c)(1),
(2) Date: Apr. 4, 2023

(87) PCT Pub. No.: WO2022/076300

PCT Pub. Date: Apr. 14, 2022

(65) Prior Publication Data

US 2023/0364325 A1     Nov. 16, 2023

Related U.S. Application Data

(60) Provisional application No. 63/088,343, filed on Oct. 6, 2020.

(51) Int. Cl.
    *G06F 21/00*       (2013.01)
    *A61M 5/00*       (2006.01)
         (Continued)

(52) U.S. Cl.
CPC ............. *A61M 5/007* (2013.01); *G06F 21/35* (2013.01); *G16H 20/17* (2018.01); *G16H 40/67* (2018.01);
         (Continued)

(58) Field of Classification Search
CPC ........ G06F 21/35; G16H 20/17; G16H 40/67; A61M 5/007
See application file for complete search history.

(56) References Cited

U.S. PATENT DOCUMENTS 3,977,391 A     8/1976    Fleischmann
6,317,623 B1    11/2001   Griffiths et al.
         (Continued)

FOREIGN PATENT DOCUMENTS

CN     114360703 A     4/2022
EP      1563859 A1     8/2005
         (Continued)

OTHER PUBLICATIONS

Charles M. Able et al., A model for preemptive maintenance of medical linear accelerators-predictive maintenance, Radiation Oncology, 2016, vol. 11/ No. 36.
         (Continued)

*Primary Examiner* — Jeffrey C Pwu
*Assistant Examiner* — Thong P Truong
(74) *Attorney, Agent, or Firm* — James R. Stevenson; Steven D. Czajkowski; Joseph L. Kent

(57) ABSTRACT

A system for securely accessing a fluid injection system is disclosed. The system includes at least one processor programmed or configured to authenticate a user for access to an fluid injection system, provide data identifying one or more features of a software application for accessing the fluid injection system, receive data identifying a selected feature of the software application for accessing the fluid
(Continued)

injection system, and provide access to the selected feature of the software application for accessing the fluid injection system.

12 Claims, 29 Drawing Sheets

(51) Int. Cl.

| | |
|---|---|
| *G06F 21/35* | (2013.01) |
| *G16H 20/17* | (2018.01) |
| *G16H 40/67* | (2018.01) |
| *A61B 5/1171* | (2016.01) |

(52) U.S. Cl.
CPC ...... *A61B 5/1171* (2016.02); *A61M 2205/502* (2013.01); *A61M 2205/60* (2013.01)

(56) References Cited

U.S. PATENT DOCUMENTS

| | | | |
|---|---|---|---|
| 6,643,537 | B1 | 11/2003 | Zatezalo et al. |
| 7,094,216 | B2 | 8/2006 | Trombley, III et al. |
| 7,457,804 | B2 | 11/2008 | Uber, III et al. |
| 7,549,977 | B2 | 6/2009 | Schriver et al. |
| 7,553,294 | B2 | 6/2009 | Lazzaro et al. |
| 7,556,619 | B2 | 7/2009 | Spohn et al. |
| 7,563,249 | B2 | 7/2009 | Schriver et al. |
| 7,766,873 | B2 | 8/2010 | Moberg et al. |
| 7,775,966 | B2 | 8/2010 | Dlugos et al. |
| 7,996,381 | B2 | 8/2011 | Uber, III et al. |
| 8,095,241 | B2 | 1/2012 | Palmerton et al. |
| 8,147,464 | B2 | 4/2012 | Spohn et al. |
| 8,337,456 | B2 | 12/2012 | Schriver et al. |
| 8,521,716 | B2 | 8/2013 | Uber, III et al. |
| 8,540,698 | B2 | 9/2013 | Spohn et al. |
| 8,945,051 | B2 | 2/2015 | Schriver et al. |
| 9,173,995 | B1 | 11/2015 | Tucker et al. |
| 9,463,335 | B2 | 10/2016 | Griffith et al. |
| 10,124,110 | B2 | 11/2018 | Dedig et al. |
| 10,507,319 | B2 | 12/2019 | Haury et al. |
| 10,549,084 | B2 | 2/2020 | Sokolov et al. |
| 10,583,256 | B2 | 3/2020 | Berry et al. |
| 2002/0070157 | A1 | 6/2002 | Yamada |
| 2003/0216692 | A1 | 11/2003 | Fago et al. |
| 2004/0138920 | A1 | 7/2004 | Sawanaga et al. |
| 2009/0070342 | A1 | 3/2009 | Uber, III et al. |
| 2009/0270810 | A1 | 10/2009 | DeBelser et al. |
| 2010/0189227 | A1 | 7/2010 | Mannar et al. |
| 2010/0305506 | A1 | 12/2010 | Fahrer |
| 2012/0110651 | A1 | 5/2012 | Van Biljon et al. |
| 2012/0209569 | A1 | 8/2012 | Becourt et al. |
| 2014/0249500 | A1 | 9/2014 | Estes |
| 2014/0266713 | A1 | 9/2014 | Sehgal et al. |
| 2015/0201912 | A1 | 7/2015 | Mercer et al. |
| 2015/0230760 | A1 | 8/2015 | Schneider |
| 2015/0374901 | A1* | 12/2015 | Kohler ................. G06Q 10/087 |
| | | | 600/432 |
| 2016/0034722 | A1 | 2/2016 | Joseph et al. |
| 2016/0213853 | A1 | 7/2016 | Despa et al. |
| 2017/0182258 | A1 | 6/2017 | Michael |
| 2018/0161496 | A1 | 6/2018 | Berry et al. |
| 2018/0240548 | A1 | 8/2018 | Spohn et al. |
| 2018/0286510 | A1 | 10/2018 | Kwan et al. |
| 2019/0050375 | A1 | 2/2019 | Fitzgibbon et al. |
| 2020/0310900 | A1 | 10/2020 | Hipp et al. |
| 2021/0272687 | A1 | 9/2021 | Klopfenstein et al. |
| 2022/0148718 | A1 | 5/2022 | Schriver et al. |

FOREIGN PATENT DOCUMENTS

| | | | |
|---|---|---|---|
| JP | 2010509984 | A | 4/2010 |
| JP | 2011516196 | A | 5/2011 |
| WO | 2008063429 | A2 | 5/2008 |
| WO | 2008064254 | A3 | 10/2008 |
| WO | 2009125398 | A2 | 10/2009 |
| WO | 2013009532 | A2 | 1/2013 |
| WO | 2013075127 | A1 | 5/2013 |
| WO | 2015106107 | A1 | 7/2015 |
| WO | 2016112163 | A1 | 7/2016 |
| WO | 2017005861 | A1 | 1/2017 |
| WO | 2017027724 | A1 | 2/2017 |
| WO | 2017040152 | A1 | 3/2017 |
| WO | 2018075386 | A1 | 4/2018 |
| WO | 2018144369 | A1 | 8/2018 |
| WO | 2019032784 | A1 | 2/2019 |
| WO | 2019035986 | A1 | 2/2019 |
| WO | 2019046261 | A1 | 3/2019 |
| WO | 2019046282 | A1 | 3/2019 |
| WO | 2021102070 | A1 | 5/2021 |
| WO | 2021222771 | A1 | 11/2021 |
| WO | 2021236472 | A1 | 11/2021 |
| WO | 2022015560 | A1 | 1/2022 |

OTHER PUBLICATIONS

From Conventional Injector to Smart Injector Brochure for EmpowerCTA Injector System, 2017.

International Preliminary Report on Patentability from PCT Application No. PCT/US2021/053359, mailed Apr. 20, 2023.

Mana Sezdi., Two Different Maintenance Strategies in the Hospital Environment: Preventive Maintenance for Older Technology Devices and Predictive Maintenance for Newer High-Tech Devices, Journal of Healthcare Engineering, Hindawi Plublishing, 2016, vol. 2016, http://dx.doi.org/10.11.55/2016/7267983.

Patil Ravindra, et al.,, Predictive Modeling for Corrective Maintenance of Imaging devices from Machine Logs, IEEE, 2017, 1676-1679.

\* cited by examiner

100

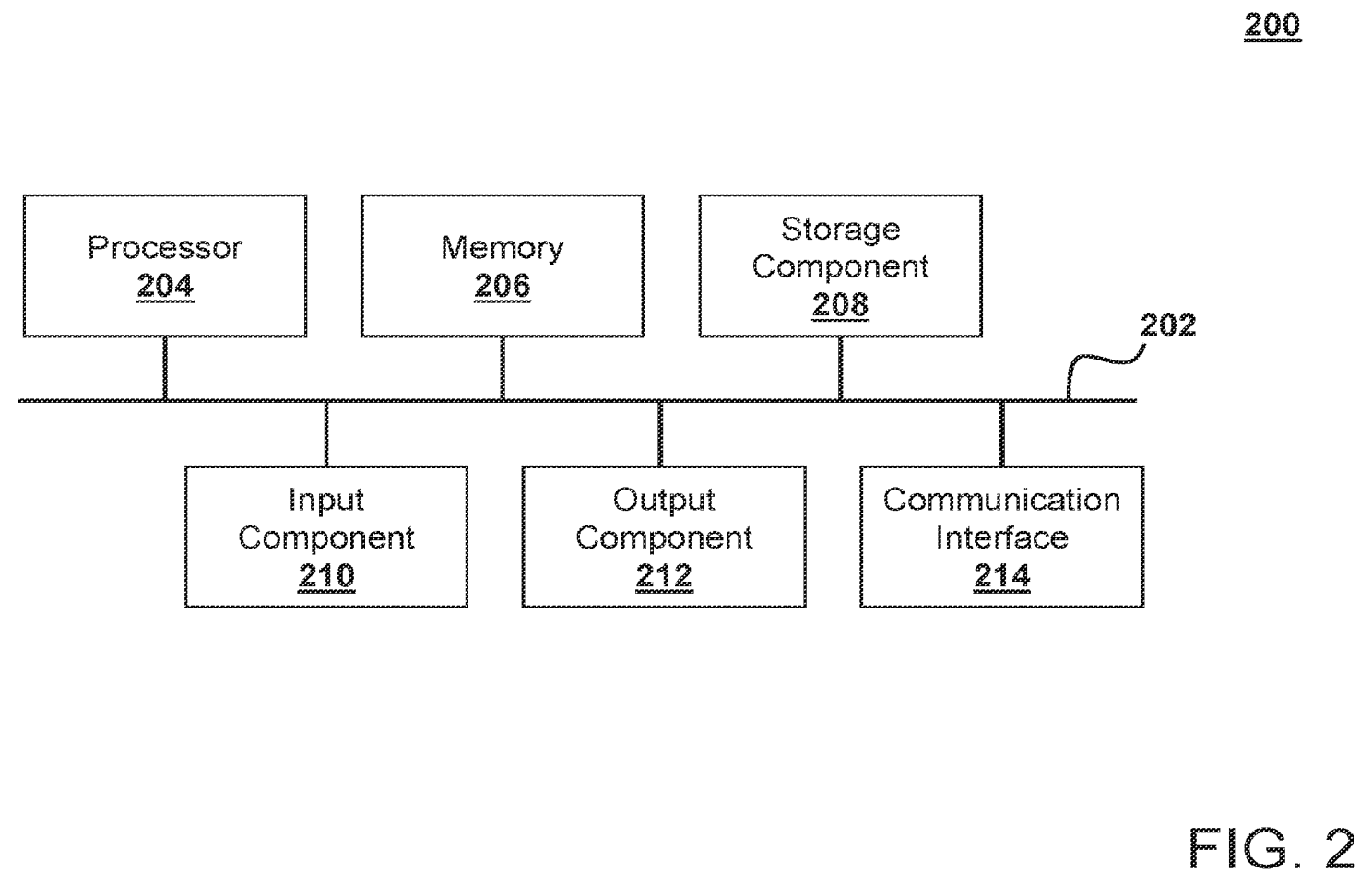

200

202

Processor
204

Memory
206

Storage
Component
208

Input
Component
210

Output
Component
212

Communication
Interface
214

FIG. 2

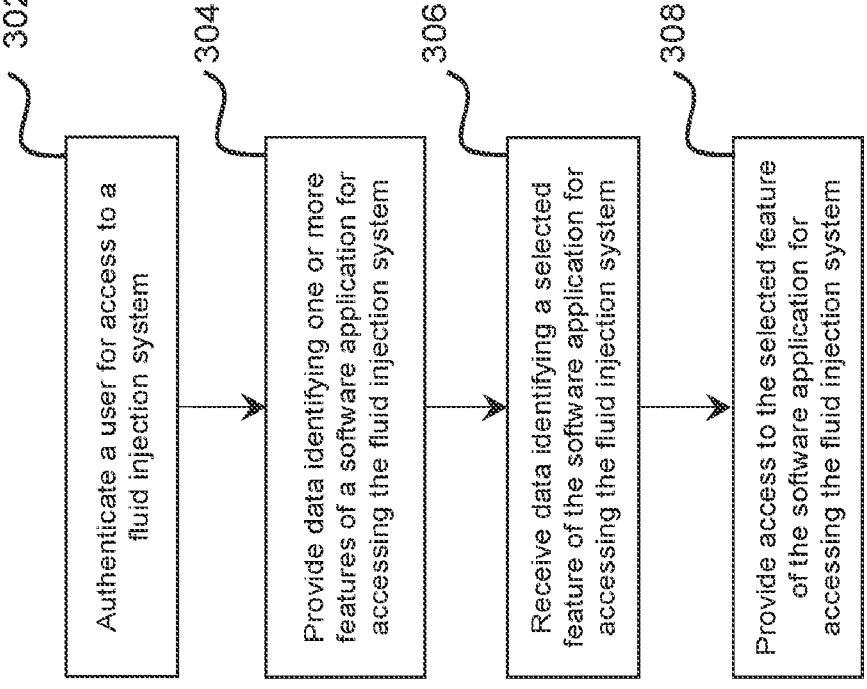

300

302 Authenticate a user for access to a fluid injection system

304 Provide data identifying one or more features of a software application for accessing the fluid injection system 306 Receive data identifying a selected feature of the software application for accessing the fluid injection system 308 Provide access to the selected feature of the software application for accessing the fluid injection system

Figure 5R:
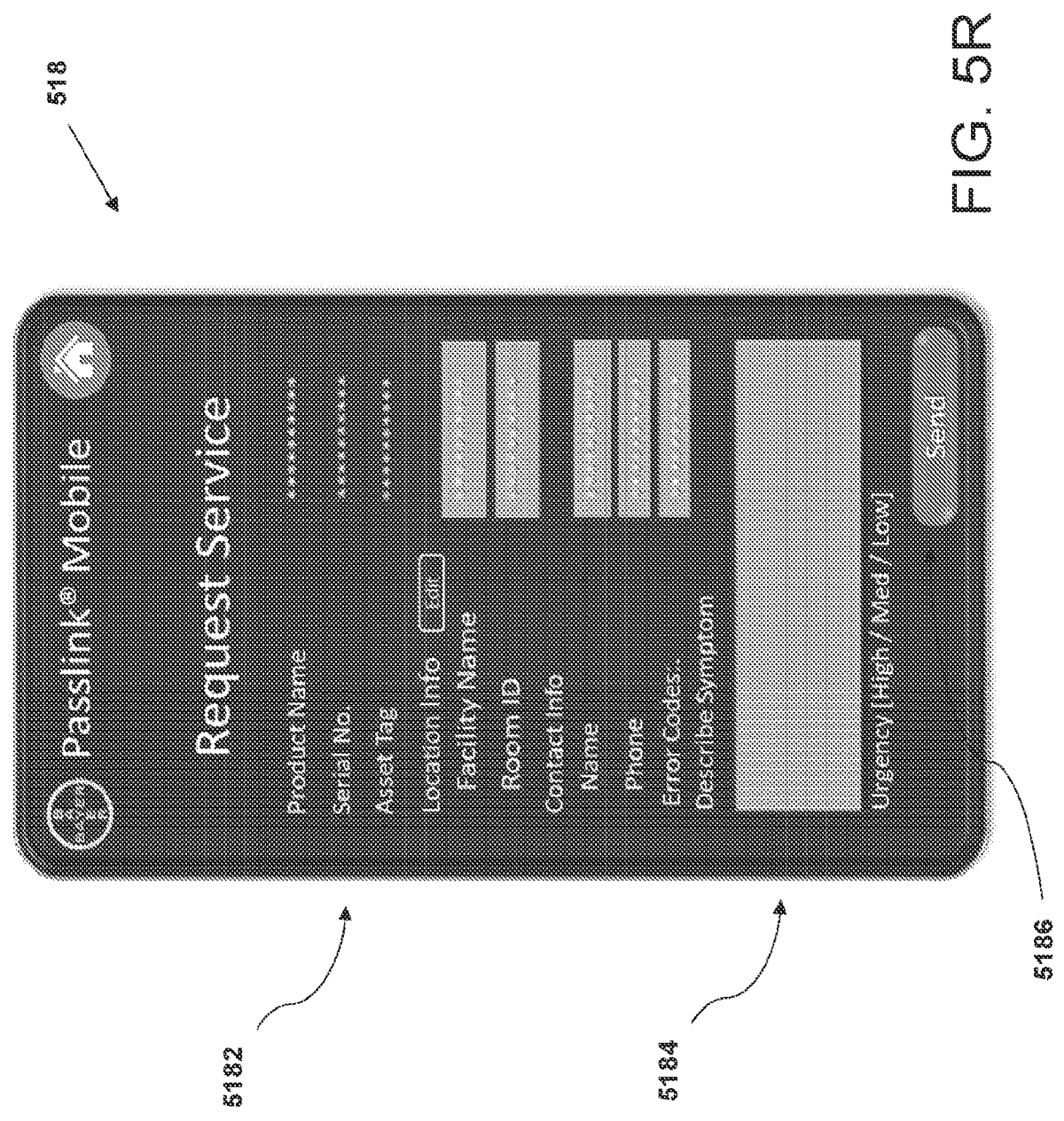

Passlink® Mobile

Request Service

Product Name
Serial No.
Asset Tag

Location Info
Facility Name
Room ID

Contact Info
Name
Phone

Error Codes
Describe Symptom

Urgency (High / Med / Low)

Edit

Send

PassInk® Mobile

Service Request Status

Request Sent
Request Confirmed
ETA (Minutes): [30]
Request Complete

Engineer
Phone
Email

Engineer Comments/Notes

5202

5204

521

PassInk® Mobile

Radiology
Medical Device
Product Report
Form

Please complete this
form and submit
within 24 hours of
notification

5212

522

5222

5224

SYSTEM, METHOD, AND COMPUTER PROGRAM PRODUCT FOR PROVIDING ACCESS TO FLUID INJECTION SYSTEMS

CROSS-REFERENCE TO RELATED APPLICATIONS

This application is a U.S. national phase application under 35 U.S.C. § 371 of International Application No. PCT/US2021/053359, filed Oct. 4, 2021 and claims the benefit of U.S. Provisional Application No. 63/088,343, filed Oct. 6, 2020, the entire disclosures of which are hereby incorporated by reference in their entirety.

BACKGROUND

1. Field

This disclosure relates generally to systems, devices, products, apparatus, and methods that provide access to an electronic device and, in one particular embodiment, to a system, product, and method for securely accessing to a fluid injection system.

2. Technical Considerations

An injection device, such as a fluid injection device (e.g., a medical fluid delivery device) may be used by a medical practitioner, such as a physician, in a medical diagnostic procedure and/or a medical therapeutic procedure. For example, the medical practitioner may use the fluid injection device to inject a patient with one or more medical fluids. The fluid injection device may be used for pressurized injection of a medical fluid, such as a radiological contrast material (e.g., a contrast agent, a radiocontrast agent, contrast media, etc.), and/or a flushing agent, such as saline, in medical imaging procedures, such as angiography, computed tomography (CT), ultrasound, magnetic resonance imaging (MRI), and positron emission tomography (PET). In some instances, the fluid injection device is designed to deliver a preset amount of a medical fluid at a preset flow rate.

In some instances, access to software of an injection device may be provided via a hardware key (e.g., a dongle, a software protection dongle, a software protection key, etc.), such as a Hardware Against Software Piracy (HASP) key. A hardware key may be an electronic copy and software content protection device. When connected to the injection device, the hardware key may be used to unlock software functionality and/or decode content. The hardware key may include (e.g., be programmed with) a product key (e.g., a software key) and/or other cryptographic protection mechanism and may allow for access to the software of the injection device when the hardware key is connected to an electrical connector, such as a universal serial bus (USB) connector, of the injection device.

SUMMARY

Accordingly, provided are systems, devices, products, apparatus, and/or methods for securely accessing a fluid injection system that improve availability of and/or accessibility to information regarding a software environment of a fluid injection system.

Further non-limiting embodiments are set forth in the following numbered clauses:

Clause 1: A system for accessing a fluid injection system comprising: at least one processor programmed or configured to: authenticate a user for access to a fluid injection system; provide data identifying one or more features of a software application for accessing the fluid injection system; receive data identifying a selected feature of the software application for accessing the fluid injection system; and provide access to the selected feature of the software application for accessing the fluid injection system.

Clause 2: The system of clause 1, wherein the at least one processor is further programmed or configured to: display the data associated with the selected feature of the software application for accessing the fluid injection system via a graphical user interface (GUI) of a mobile application on a user device.

Clause 3: The system of clauses 1 or 2, wherein the at least one processor is further programmed or configured to: determine whether the user is authorized to access the selected feature of the software application for accessing the fluid injection system based on authenticating the user for access to the fluid injection system.

Clause 4: The system of any of clauses 1-3, wherein, when determining whether the user is authorized to access selected feature of the software application for accessing the fluid injection system, the at least one processor is programmed or configured to: determine whether the user has a level of access that authorizes the user to access the selected feature of the software application for accessing the fluid injection system.

Clause 5: The system of any of clauses 1-4 wherein the fluid injection system comprises a display screen, and wherein the at least one processor is further programmed or configured to: cause data associated with the fluid injection system to be displayed on the display screen of the fluid injection system.

Clause 6: The system of any of clauses 1-5, wherein the at least one processor is further programmed or configured to: access the selected feature of the software application of the fluid injection system to provide data associated with the fluid injection system, wherein the data associated with the fluid injection system comprises data associated with one or more operations of the fluid injection system; and wherein the at least one processor is further programmed or configured to: log the data associated with one or more operations of the fluid injection system.

Clause 7: The system of any of clauses 1-6, wherein, when providing access to the selected feature of the software application for accessing the fluid injection system, the at least one processor is programmed or configured to: provide access to the selected feature of the software application for accessing the fluid injection system based on determining that the user is authorized to access the selected feature of the software application.

Clause 8: A computer program product for accessing a fluid injection system, the computer program product comprising at least one non-transitory computer-readable medium including one or more instructions that, when executed by at least one processor, cause the at least one processor to: authenticate a user for access to a fluid injection system; provide data identifying one or more features of a software application for accessing the fluid injection system; receive data identifying a selected feature of the software application of the fluid injection system; and provide access to the selected feature of the software application of the fluid injection system.

Clause 9: The computer program product of clause 8, wherein the one or more instructions further cause the at least one processor to: display data associated with the selected feature of the software application of the fluid injection system via a graphical user interface (GUI) of a mobile application on a user device.

Clause 10: The computer program product of clauses 8 or 9, wherein the one or more instructions further cause the at least one processor to: determine whether the user is authorized to access the selected feature of the software application of the fluid injection system based on authenticating the user for access to the fluid injection system.

Clause 11: The computer program product of any of clauses 8-10, wherein the one or more instructions that cause the at least one processor to determine whether the user is authorized to access the selected feature of the software application for accessing the fluid injection system further cause the at least one processor to: determine whether the user has a level of access that authorizes the user to access the selected feature of the software application for accessing the fluid injection system.

Clause 12: The computer program product of any of clauses 8-11, wherein the fluid injection system comprises a display screen, and wherein the one or more instructions further cause the at least one processor to: cause data associated with the fluid injection system to be displayed on the display screen of the fluid injection system.

Clause 13: The computer program product of any of clauses 8-12, wherein the one or more instructions further cause the at least one processor to: access the selected feature of the software application for accessing the fluid injection system to provide data associated with the fluid injection system, wherein the data associated with the fluid injection system comprises data associated with one or more operations of the fluid injection system; and wherein the one or more instructions further cause the at least one processor to: log the data associated with the one or more operations of the fluid injection system.

Clause 14: The computer program product of any of clauses 8-13, wherein the one or more instructions that cause the at least one processor to provide access to the selected feature of the software application for accessing the fluid injection system further cause the at least one processor to: provide access to the selected feature of the software application for accessing the fluid injection system based on determining that the user is authorized to access the selected feature of the software application for accessing the fluid injection system.

Clause 15: A method for accessing a fluid injection system comprising: authenticating, with at least one processor, a user for access to a fluid injection system; providing, with the at least one processor, data identifying one or more features of a software application for accessing the fluid injection system; receiving, with the at least one processor, data identifying a selected feature of the software application for accessing the fluid injection system; and providing, with the at least one processor, access to the selected feature of the software application for accessing the fluid injection system.

Clause 16: The method of clause 15, further comprising: displaying data associated with the selected feature of the software application of the fluid injection system via a graphical user interface (GUI) of a mobile application on a user device.

Clause 17: The method of clauses 15 or 16, further comprising: determining whether the user is authorized to access the selected feature of the software application for accessing the fluid injection system based on authenticating the user for access to the fluid injection system.

Clause 18: The method of any of clauses 15-17, wherein determining whether the user is authorized to access the selected feature of the software application for accessing the fluid injection system comprises: determining whether the user has a level of access that authorizes the user to access the selected feature of the software application for accessing the fluid injection system.

Clause 19: The method of any of clauses 15-18, wherein the fluid injection system comprises a display screen, and wherein the method further comprises: causing data associated with the fluid injection system to be displayed on a display screen of the fluid injection system.

Clause 20: The method of any of clauses 15-19, further comprising: accessing the selected feature of the software application for accessing the fluid injection system to provide data associated with the fluid injection system, wherein the data associated with the fluid injection system comprises data associated with one or more operations of the fluid injection system; and wherein the method further comprises: logging the data associated with the one or more operations of the fluid injection system.

Clause 21: The method of any of clauses 15-20, wherein providing access to the selected feature of the software application for accessing the fluid injection system comprises: providing access to the selected feature of the software application for accessing the fluid injection system based on determining that the user is authorized to access the selected feature of the software application.

These and other characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present disclosure. As used in the specification and the claims, the singular form of "a," "an," and "the" include plural referents unless the context clearly dictates otherwise.

BRIEF DESCRIPTION OF THE DRAWINGS

Additional advantages and details of the present disclosure are explained in greater detail below with reference to the exemplary embodiments that are illustrated in the accompanying schematic figures, in which:

FIG. 2 is a diagram of a non-limiting embodiment of components of one or more systems or one or more devices of FIG. 1;

FIG. 3 is a flowchart of a non-limiting embodiment of a process for securely accessing a fluid injection system;

DETAILED DESCRIPTION

Figure 1:
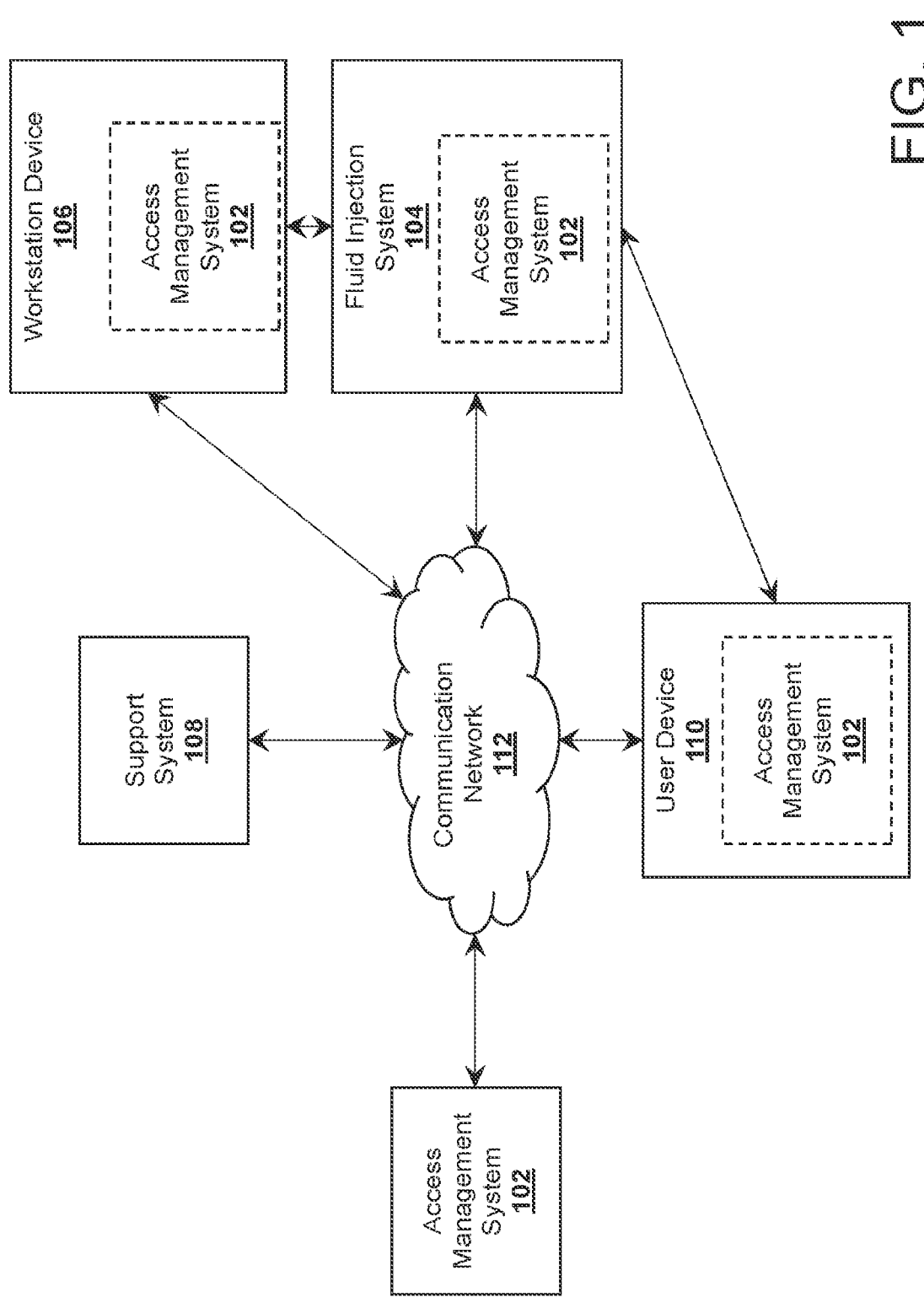
FIG. 1 is a diagram of a non-limiting embodiment of an environment in which systems, devices, products, apparatus, and/or methods, described herein, may be implemented according to the principles of the present disclosure.

For purposes of the description hereinafter, the terms "end," "upper," "lower," "right," "left," "vertical," "horizontal," "top," "bottom," "lateral," "longitudinal," and derivatives thereof shall relate to the present disclosure as it is oriented in the drawing figures. However, it is to be understood that the present disclosure may assume various alternative variations and step sequences, except where expressly specified to the contrary. It is also to be understood that the specific devices and processes illustrated in the attached drawings, and described in the following specification, are simply exemplary embodiments of the present disclosure. Hence, specific dimensions and other physical characteristics related to the embodiments of the embodiments disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the terms "communication" and "communicate" may refer to the reception, receipt, transmission, transfer, provision, and/or the like of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments, a message may refer to a network packet (e.g., a data packet and/or the like) that includes data. It will be appreciated that numerous other arrangements are possible.

As used herein, the term "system" may refer to one or more computing devices or combinations of computing devices such as, but not limited to, processors, servers, client devices, software applications, and/or other like components. In addition, reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

In some instances, a fluid injection device may be part of a group of devices that are used in a medical treatment facility, such as a hospital, during treatment of patients. Individuals, such as technicians (e.g., field service engineers), administrative personnel, or others who are properly trained with regard to operation of the fluid injection device, may access software of the fluid injection device via a hardware key. In some examples, an individual may access service related software tools via the hardware key. In one example, the fluid injection device may malfunction during a fluid injection operation and the individual may obtain information regarding the malfunction by connecting the hardware key to the fluid injection device and downloading a report that includes the information. In addition, the individual may install software updates to the fluid injection device, including product feature enhancements, operating system updates, and/or security updates (e.g., security patches), for example, via use of the hardware key.

However, an individual may be required to have possession of the hardware key to access the fluid injection device and the physical nature of the hardware key lends it to the possibility of loss, damage, theft, and/or the like. In addition, multiple hardware keys may be associated with a specific fluid injection device, such that more than one key is necessary to access all software functionality of that fluid injection device. Further, the product key associated with a hardware key may expire following a period of time for a user license and, as part of a renewal process of the user license, an operator of the fluid injection device may be required to obtain and provide identification information for the fluid injection device. The process of obtaining and providing the identification information for the fluid injection device may be resource and labor intensive on behalf of the operator. In a similar fashion, as components of the fluid injection device are maintained and/or replaced, the product key may be required to be updated on the hardware key before the hardware key is able to access the software functionality of the fluid injection device.

Non-limiting embodiments of the present disclosure are directed to systems, devices, products, apparatus, and/or methods for securely accessing a fluid injection system. In some non-limiting embodiments, an access management system may include at least one processor programmed or configured to authenticate a user for access to an fluid injection system; provide data identifying one or more features of a software application for accessing the fluid injection system; receive data identifying a selected feature of the software application for accessing the fluid injection system; and provide access to the selected feature of the software application for accessing the fluid injection system. In some non-limiting embodiments, the at least one processor is further programmed or configured to display data associated with the selected feature of the software application for accessing the fluid injection system via a graphical user interface (GUI) of a mobile application on a user device. in some non-limiting embodiments, the at least one processor is further programmed or configured to determine whether the user is authorized to access the selected feature of the software application for accessing the fluid injection system based on authenticating the user for access to the fluid injection system. In some non-limiting embodiments, when determining whether the user is authorized to access selected feature of the software application for accessing the fluid injection system, the at least one processor is programmed or configured to determine whether the user has a level of access that authorizes the user to access the selected feature of the software application for accessing the fluid injection system.

In some non-limiting embodiments, the fluid injection system comprises a display screen, and the at least one processor is further programmed or configured to cause data associated with the fluid injection system to be displayed on the display screen of the fluid injection system. In some non-limiting embodiments, the at least one processor is further programmed or configured to access the selected feature of the software application of the fluid injection system to provide data associated with the fluid injection system, wherein the data associated with the fluid injection system comprises data associated with one or more operations of the fluid injection system; and the at least one processor is further programmed or configured to log the data associated with one or more operations of the fluid injection system. In some non-limiting embodiments, when providing access to the selected feature of the software application for accessing the fluid injection system, the at least one processor is programmed or configured to provide access to the selected feature of the software application for accessing the fluid injection system based on determining that the user is authorized to access the selected feature of the software application.

In this way, non-limiting embodiments of the present disclosure provide for readily available access to a fluid injection system and information associated with the fluid injection system. Furthermore, non-limiting embodiments of the present disclosure eliminate the need for a hardware key to be used to access the fluid injection system. In this way, non-limiting embodiments of the present disclosure also eliminate the need for updating information that is stored on the hardware key, including a product key to access the software functionality of the fluid injection device.

Referring now to FIG. 1, FIG. 1 is a diagram of an example environment 100 in which devices, systems, and/or methods, described herein, may be implemented. As shown in FIG. 1, environment 100 includes access management system 102, fluid injection system 104, workstation device 106, support system 108, user device 110, and communication network 112. In some non-limiting embodiments, access management system 102, fluid injection system 104, workstation device 106, support system 108, and/or user device 110 may interconnect (e.g., establish a connection to communicate) via wired connections, wireless connections, or a combination of wired and wireless connections.

In some non-limiting embodiments, access management system 102 includes one or more devices capable of being in communication with fluid injection system 104, workstation device 106, support system 108, and/or user device 110 via communication network 112. For example, access management system 102 can include a computing device, such as a computer, a server, a group of servers, and/or other like devices. In some non-limiting embodiments, access management system 102 may be a component of fluid injection system 104 and/or workstation device 106.

In some non-limiting embodiments, fluid injection system 104 includes one or more devices capable of being in communication with access management system 102, workstation device 106, support system 108, and/or user device 110 via communication network 112. For example, fluid injection system 104 can include a computing device, such as one or more computers, a server, a group of servers, and/or other like devices. In some non-limiting embodiments, fluid injection system 104 includes one or more injection devices (e.g., one or more fluid injection devices). In some non-limiting embodiments, fluid injection system 104 is configured to administer (e.g., inject, deliver, etc.) contrast fluid including a contrast agent to a patient, and/or administer an aqueous fluid, such as saline, to a patient before, during, and/or after administering the contrast fluid. For example, fluid injection system 104 can inject one or more prescribed dosages of contrast fluid directly into a patient's blood stream via a hypodermic needle and syringe. In some non-limiting embodiments, fluid injection system 104 may be configured to continually administer the aqueous fluid to a patient through a peripheral intravenous line (PIV) and catheter, and one or more prescribed dosages of contrast fluid may be introduced into the PIV and administered via the catheter to the patient. In some non-limiting embodiments, fluid injection system 104 is configured to inject a dose of contrast fluid followed by administration of a particular volume of the aqueous fluid. In some non-limiting embodiments, fluid injection system 104 may include a device capable of reading (e.g., scanning) a barcode, such as a quick response (QR) code.

In some non-limiting embodiments, fluid injection system 104 may include one or more exemplary injection systems or injectors that are disclosed in: U.S. patent application Ser. No. 09/715,330, filed on Nov. 17, 2000, issued as U.S. Pat. No. 6,643,537; U.S. patent application Ser. No. 09/982,518, filed on Oct. 18, 2001, issued as U.S. Pat. No. 7,094,216; U.S. patent application Ser. No. 10/825,866, filed on Apr. 16, 2004, issued as U.S. Pat. No. 7,556,619; U.S. patent application Ser. No. 12/437,011, filed May 7, 2009, issued as U.S. Pat. No. 8,337,456; U.S. patent application Ser. No. 12/476, 513, filed Jun. 2, 2009, issued as U.S. Pat. No. 8,147,464; and U.S. patent application Ser. No. 11/004,670, filed on Dec. 3, 2004, issued as U.S. Pat. No. 8,540,698, the disclosures of each of which are incorporated herein by reference in their entireties. In some non-limiting embodiments, fluid injection system 104 may include the MEDRAD® Stellant CT Injection System, the MEDRAD® Stellant FLEX CT Injection System, MEDRAD® Spectris Solaris EP MR Injection System, the MEDRAD® MRXperion MR Injection System, MEDRAD® Salient Contrast Injection System, the MEDRAD® Mark 7 Arterion Injection System, MEDRAD® Avanta Fluid Management Injection System, the MEDRAD® Intego PET Infusion System, or the MEDRAD® Centargo CT Injection System, all of which are provided by Bayer.

In some non-limiting embodiments, workstation device 106 includes one or more devices capable of being in communication with access management system 102, fluid injection system 104, support system 108, and/or user device 110 via communication network 112. For example, workstation device 106 may include a computing device, such as one or more computers, including a desktop computer, a laptop, a tablet, and/or the like. In some non-limiting embodiments, workstation device 106 may provide a control interface for controlling operation of fluid injection system 104, including providing inputs to fluid injection system 104. Additionally or alternatively, workstation device 106 may display operational parameters of fluid injection system 104 during operation (e.g., during real-time operation) of fluid injection system 104. In some non-limiting embodiments, workstation device 106 may provide interconnectivity between fluid injection system 104 and other devices or systems, such as a scanner device (not shown). In some non-limiting embodiments, workstation device 106 may include the Certegra® Workstation provided by Bayer.

In some non-limiting embodiments, support system 108 may include one or more devices capable of being in communication with access management system 102, fluid injection system 104, workstation device 106, and/or user device 110 via communication network 112. For example, remote system 108 may include a computing device, such as a computer, a server (e.g., a web server), a group of servers, and/or other like devices. In some non-limiting embodiments, support system 108 may include a back-end system associated with access management system 102, fluid injection system 104, and/or workstation device 106. In some non-limiting embodiments, support system 108 may include a cloud computing system that stores data in an associated database. In some non-limiting embodiments, support system 108 may be capable of interacting with fluid injection system 104 to provide functionality, such as remote equipment service for fluid injection system 104 (e.g., Virtual-CARE® remote equipment support service for injection systems and devices provided by Bayer). In some non-limiting embodiments, support system 108 may be operated by or on behalf of an original equipment manufacturer (OEM) of fluid injection system 104 (e.g., an OEM of one or more components or devices of fluid injection system 104), a provider of fluid injection system 104, an imaging site or a hospital in which fluid injection system 104 is operated, a service technician assigned to fluid injection system 104, and/or the like. In some non-limiting embodiments, support system 108 may include a hospital information system (HIS), a radiology information system (RIS) and/or the like. In some non-limiting embodiments, support system 108 may include a customer relationship management (CRM) system.

In some non-limiting embodiments, user device 110 may include one or more devices capable of being in communication with access management system 102, fluid injection system 104, workstation device 106, and/or support system 108 via communication network 112. For example, user device 110 may include a computing device, such as a computer (e.g., a desktop, a laptop, etc.) or a mobile device (e.g., a smart phone, a tablet, etc.). In some non-limiting embodiments, user device 110 may be capable of reading (e.g., scanning) a barcode, such as a quick response (QR) code. In some non-limiting embodiments, user device 110 may be configured to transmit and/or receive data to and/or from another device or system (e.g., fluid injection system 104, workstation device 106) via a short-range wireless communication connection (e.g., an NFC communication connection, an RFID communication connection, a Bluetooth® communication connection, and/or the like). In some non-limiting embodiments, user device 110 may be configured to transmit and/or receive data via radio frequency identification (RFID). For example, user device 110 may include an RFID reader. In some non-limiting, user device 110 may be associated with a user (e.g., an individual operating a device). In some non-limiting embodiments, one or more software (e.g., mobile) applications may be associated with (e.g., installed and/or executed on) user device 110 (e.g., an application stored on user device 110, such as a mobile device application, a native application for a mobile device, a mobile cloud application for a mobile device, etc.).

In some non-limiting embodiments, communication network 112 may include one or more wired and/or wireless networks. For example, communication network 112 may include a cellular network (e.g., a long-term evolution (LTE) network, a third generation (3G) network, a fourth generation (4G) network, a fifth generation (5G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, a short range wireless communication network (e.g., a Bluetooth® network, a near field communication (NFC) network, etc.) and/or the like, and/or a combination of these or other types of networks.

The number and arrangement of systems, devices, and networks shown in FIG. 1 are provided as an example. There may be additional systems and/or devices, fewer systems and/or devices, different systems and/or devices, and/or differently arranged systems and/or devices than those shown in FIG. 1. Furthermore, two or more systems or devices shown in FIG. 1 may be implemented within a single system or a single device, or a single system or a single device shown in FIG. 1 may be implemented as multiple, distributed systems or devices. Additionally, or alternatively, a set of systems or a set of devices (e.g., one or more systems, one or more devices, etc.) of environment 100 may perform one or more functions described as being performed by another set of systems or another set of devices of environment 100.

Referring now to FIG. 2, FIG. 2 is a diagram of example components of a device 200. Device 200 may correspond to one or more devices of access management system 102, one or more devices of fluid injection system 104, workstation device 106, one or more devices of support system 108, and/or user device 110. In some non-limiting embodiments, access management system 102, fluid injection system 104, workstation device 106, support system 108, and/or user device 110 can include at least one device 200 and/or at least one component of device 200. As shown in FIG. 2, device 200 may include bus 202, processor 204, memory 206, storage component 208, input component 210, output component 212, and communication interface 214.

Bus 202 may include a component that permits communication among the components of device 200. In some non-limiting embodiments, processor 204 may be implemented in hardware, software, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read only memory (ROM), and/or another type of dynamic or static storage device (e.g., flash memory, magnetic memory, optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally, or alternatively, input component 210 may include a sensor for sensing information (e.g., a global positioning system (GPS) component, an accelerometer, a gyroscope, an actuator, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmitter, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software.

The number and arrangement of components shown in FIG. 2 are provided as an example. In some non-limiting embodiments, device 200 may include additional components, fewer components, different components, or differently arranged components than those shown in FIG. 2. Additionally or alternatively, a set of components (e.g., one or more components) of device 200 may perform one or more functions described as being performed by another set of components of device 200.

Referring now to FIG. 3, FIG. 3 is a flowchart of a non-limiting embodiment of a process 300 for securely accessing a fluid injection system. In some non-limiting embodiments, one or more of the steps of process 300 are performed (e.g., completely, partially, etc.) by access management system 102 (e.g., one or more devices of access management system 102, etc.). In some non-limiting embodiments, one or more of the steps of process 300 are performed (e.g., completely, partially, etc.) by another device or a group of devices separate from or including access management system 102, such as fluid injection system 104 (e.g., one or more devices of fluid injection system 104, etc.), workstation device 106, support system 108 (e.g., one or more devices of support system 108, etc.), and/or user device 110.

Aspects (e.g., one or more of the steps of process 300) of non-limiting embodiments herein may be performed with regard to a software application, such as a mobile application, with a client-side component stored on user device 110 that is associated with a server-side component of access management system 102. In some non-limiting embodiments, the software application may be operated by (e.g., controlled by) access management system 102 to access one or more features of a software environment (e.g., one or more software applications of a software environment, one or more software services of a software environment, one or more software tools of a software environment, etc.) of fluid injection system 104. Additionally or alternatively, one or more aspects of the software application may be stored on fluid injection system 104 and/or workstation device 106. In some non-limiting embodiments, one or more features of the software application may provide access to the one or more features of the software environment of fluid injection system 104.

In some non-limiting embodiments, the one or more features of the software environment of fluid injection system 104 may include a feature associated with a patient procedure tracking system (e.g., a system that operates a modality worklist, a system that provides patient demographic information for fluid injection procedures and/or medical imaging procedures, etc.), a feature associated with a fluid injector management system, a feature associated with an image archive and communication system (e.g., a picture archive and communication system (PACS)), a feature associated with a radiology information system (RIS), and/or a feature associated with a radiology analytics system (e.g., the Radimetrics® Enterprise Application marketed and sold by Bayer HealthCare LLC).

As shown in FIG. 3, at step 302, process 300 includes authenticating a user for access to a fluid injection system. For example, access management system 102 may authenticate the user for access to fluid injection system 104 via a software application for accessing fluid injection system 104 stored on user device 110. Access management system 102 may authenticate the user for access to fluid injection system 104 via the software application independent of (e.g., without) a hardware key. In some non-limiting embodiments, access management system 102 may receive data associated with user identification from a user via user device 110 (e.g., a software application for accessing fluid injection system 104 stored on user device 110) during a login process and access management system 102 may use the data associated with user identification for authentication of the user for access to fluid injection system 104 (e.g., access to one or more features of a software application for accessing fluid injection system 104). In some non-limiting embodiments, access management system 102 may generate a graphical user interface (GUI) and provide the GUI for display on user device 110 to receive user input as part of the login process. The user input may include a login credential. In some non-limiting embodiments, the login credential may include data associated with user identification, such as data identifying a username, a password, an employee identification number, a device identifier (e.g., Internet Protocol (IP) address, media access control (MAC) address, etc.), a phone number, an office location, an office address, and/or the like. In some non-limiting embodiments, the login credential may include a biometric measurement of a user (e.g., a fingerprint, an iris scan, an image of a body part of a user, etc.). In some non-limiting embodiments, access management system 102 may authenticate the user for access to a software application for accessing fluid injection system 104 and access management system 102 may determine whether the user is authorized to access one or more features of the software application based on authenticating the user.

In some non-limiting embodiments, access management system 102 may generate the login credential for providing to fluid injection system 104 to authenticate the user for access to fluid injection system 104. For example, access management system 102 may generate the login credential (e.g., a password, a passcode, etc.) based on a clock (e.g., an internal clock of user device 110). In some non-limiting embodiments, access management system 102 may provide a GUI on fluid injection system 104 or workstation device 106 (e.g., on a display screen of fluid injection system 104 or workstation device 106) to display an indicator and access management system 102 may receive a login credential associated with the indicator from user device 110 via the software application. For example, access management system 102 may provide the GUI on a display screen of fluid injection system 104 or workstation device 106 that displays an image (e.g., an image of a QR code) and user device 110 may scan the image. User device 110 may determine a login credential associated with the image and user device 110 may provide the login credential to access management system 102 via the software application. Access management system 102 may authenticate the user for access to fluid injection system 104 based on receiving the login credential via the software application. In some non-limiting embodiments, access management system 102 may provide a GUI on user device 110 to display an indicator and access management system 102 may receive a login credential associated with the indicator from fluid injection system 104 via the software application. For example, access management system 102 may provide the GUI on a display screen of user device 110 that displays an image (e.g., an image of a QR code) and fluid injection system 104 may scan the image. Fluid injection system 104 may determine a login credential associated with the image and fluid injection system 104 may provide the login credential to access management system 102 via the software application. Access management system 102 may authenticate the user for access to fluid injection system 104 based on receiving the login credential via the software application.

In some non-limiting embodiments, access management system 102 may receive the login credential from fluid injection system 104 to authenticate the user for access to fluid injection system 104. For example, access management system 102 may provide the login credential to a user (e.g., via user device) and the user may input the login credential to fluid injection system 104. Fluid injection system may transmit the login credential to access management system 102 and access management system 102 may authenticate the user for access to fluid injection system 104 based on receiving the login credential.

In some non-limiting embodiments, the features (e.g., services, tools, etc.) of the software application for accessing fluid injection system 104 may include one or more features associated with providing data associated with fluid injection system 104. In some non-limiting embodiments, access management system 102 may communicate with a web application (e.g., communicate with a web application operated by a web server) to obtain data associated with fluid injection system 104 via the software application. For example, access management system 102 may communicate with the web application to obtain data associated with a user profile, data associated with a user license (e.g., a software license for a user), and/or the like.

In some examples, the data associated with fluid injection system 104 may include data associated with an identifier of fluid injection system 104 (e.g., a device identifier of fluid injection system 104, a model number of fluid injection system 104, a serial number of fluid injection system 104, etc.), data associated with software or hardware of fluid injection system 104 (e.g., a software configuration of fluid injection system 104, a hardware configuration of fluid injection system 104, a software version of fluid injection system 104, such as a software version of an operating system of fluid injection system 104, a revision number of software of fluid injection system 104, an identifier of one or more software patches that have been applied to fluid injection system 104, etc.), and/or data associated with a network connection of fluid injection system 104 (e.g., a MAC address of a network interface controller (NIC) of fluid injection system 104, an IP address of fluid injection system 104, etc.). In some non-limiting embodiments, the data associated with fluid injection system 104 may include data associated with one or more operations of fluid injection system 104. The data associated with one or more operations of fluid injection system 104 may include data associated with operations carried out by fluid injection system 104 (e.g., a number of fluid injection operations carried out by fluid injection system 104, times of fluid injection operations carried out by fluid injection system 104, operational parameters of fluid injection operations carried out by fluid injection system 104, data associated with patient demographics for patients upon which fluid injection operations were carded out by fluid injection system 104, etc.), data associated with a configuration of fluid injection system 104 (e.g., a configuration of fluid delivery components of fluid injection system 104, a cyber-security bill of materials (CBOM) of fluid injection system 104, a software bill of materials (SBOM) of fluid injection system 104, etc.), and/or data associated with a malfunction encountered during one or more operations of fluid injection system 104. In some non-limiting embodiments, access management system 102 may log (e.g., store in a data log) the data associated with fluid injection system 104. For example, access management system 102 may log the data associated with one or more operations of fluid injection system 104. It is noted that embodiments of the present disclosure comply with all legal requirements, for example, the Health Insurance Portability and Accountability Act (HIPAA), such that data associated with fluid injection system 104 that is stored or communicated may not include personal health information of patients, such as PHI and PII, as appropriate.

In some non-limiting embodiments, operational parameters of fluid injection operations carried out by fluid injection system 104 may include one or more exemplary data types that are disclosed in U.S. patent application Ser. No. 10/143,562, filed on May 10, 2002, issued as U.S. Pat. No. 7,457,804; U.S. patent application Ser. No. 12/254,318, filed on Oct. 20, 2008, issued as U.S. Pat. No. 7,996,381; U.S. patent application Ser. No. 13/180,175, filed on Jul. 11, 2011, issued as U.S. Pat. No. 8,521,716, the disclosures of each of which are incorporated herein by reference in their entireties.

In some non-limiting embodiments, the data associated with a malfunction encountered during one or more operations of fluid injection system 104 may include an identifier of an error associated with an operation of fluid injection system 104. The identifier of the error associated with the operation of fluid injection system 104 may include an error code (e.g., a specific error code associated with the type of malfunction encountered). Additionally or alternatively, the data associated with a malfunction encountered during one or more operations of fluid injection system 104 may include operational parameters of fluid injection system 104 associated with the malfunction. For example, the data associated with a malfunction encountered during one or more operations of fluid injection system 104 may include a temperature measurement of a component of fluid injection system 104, a pressure measurement associated with a component (e.g., a disposable such as a multiple use disposable set (MUDS), a single use disposable set (SUDS), a syringe or a tubing set) used with fluid injection system 104, a measurement of an electrical characteristic (e.g., voltage, current, power, etc.) of electrical components of fluid injection system 104, and/or other relevant values of variables and/or system components.

In some non-limiting embodiments, the features of the software application for accessing fluid injection system 104 may include a feature associated with obtaining (e.g., reading, scanning, retrieving from a data structure, etc.) data associated with an error code of (e.g., an error code generated by) fluid injection system 104, a feature associated with determining a location (e.g., a location based on a global positioning system (GPS) location) of fluid injection system 104, a feature associated with generating a service history of fluid injection system 104, a feature associated with providing (e.g., providing for download, displaying, printing, transmitting a message that includes, etc.) a service history of fluid injection system 104, a feature associated with providing a list of assets (e.g., a plurality of fluid injection systems 104, one or more components of fluid injection system 104, components of a plurality of fluid injection systems 104, etc.), a feature associated with adding an asset to a list of assets, a feature associated with providing a list of features of a software environment of fluid injection system 104 that are covered by a user license, a feature associated with initiating billing (e.g., automatic billing) for one or more features of a software environment of fluid injection system 104 that are covered by a user license, a feature associated with adding one or more features (e.g., an equipment support service, such as VirtualCARE® Remote Support which permits secure and reliable remote monitoring of its contrast media injection systems and software to minimize downtime; SelectCARE®, PartnerCARE®, and DirectCARE® service agreement programs which offer increasing levels of service and capabilities including VirtualCARE®; TechCARE®; and TechCARE® NxT non-obsolescence programs which also include the services and capabilities offered through service agreement programs, by Bayer) of a software environment of fluid injection system 104 to a user license, a feature associated with generating a service request for fluid injection system 104, a feature associated with registering a warranty, a feature associated with providing data associated with consumables (e.g., a multiple use disposable set (MUDS), a single use disposable set (SUDS), a syringe or a tubing set) used during fluid injection procedures, a feature associated with providing a list of one or more fluid injection protocols to fluid injection system 104, a feature associated with adding or restoring (e.g., restoring following a service procedure) one or more fluid injection protocols to fluid injection system 104, a feature associated with providing and/or receiving data regarding user preferences (e.g., user preferences associated with look and feel of the software application, such as display colors and/or languages of data provided), a feature associated with providing software (e.g., with providing an operating system) to a software environment of fluid injection system 104, a feature associated with providing instructions for operation of fluid injection system 104, a feature associated with providing data associated with a service procedure (e.g., data associated with diagnosing and/or troubleshooting capabilities for service procedures, such as augmented reality (AR) capabilities for service procedures, real-time data associated with aspects of components of fluid injection system 104, such as calibration values, fluids, batteries, motors, etc.) to be performed on fluid injection system 104, a feature associated with providing data associated with a service procedure (e.g., a service report based on a service procedure, a final checklist following a service procedure, a message that includes confirmation of completion of a service procedure, etc.) that was performed on fluid injection system 104, and/or a feature associated with providing a complaint regarding a product.

In some non-limiting embodiments, the feature associated with providing the list of assets may include a feature associated with providing the list of assets associated with a user license. In some non-limiting embodiments, the feature may provide for the list of assets associated with the user license to be provided according to an encryption protocol. In some non-limiting embodiments, the list of assets may include identifiers of scan room units (SRUs) and control room units (CRUs) IDs. In some non-limiting embodiments, the list of assets may be organized (e.g., ranked) based on a user preference. In some non-limiting embodiments, the feature may provide for (e.g., provide for download, display, print, transmit a message that includes, etc.) a report (e.g., service report) associated with the list of assets (e.g., a report that includes data associated with each asset in the list of assets, one or more assets in the list of assets, etc.) associated with a user license. In some non-limiting embodiments, the feature may provide for transmitting the report to a system (e.g., a service management system, a flight recorder system, etc.) external to fluid injection system 104. In some non-limiting embodiments, the feature may provide data associated with each of the assets, including a software configuration (e.g., a current software level), calibration date (e.g., most recent calibration date, all calibration dates, etc.), a user that performed a calibration, and aspects of an asset that were calibrated (e.g., pressure, potentiometers, etc.).

In some non-limiting embodiments, the feature associated with providing software to a software environment of fluid injection system 104 may provide software uploads, such as updates (e.g., patches), to and additional features for the software environment of fluid injection system 104, and/or the like, and/or software downloads from the software environment of fluid injection system 104. For example, the feature may provide software uploads to and/or software downloads from the software environment of fluid injection system 104 when connectivity to communication network 112 is not available via the software application for accessing fluid injection system 104. In some non-limiting embodiments, a software upload may be stored (e.g., preloaded) on user device 110 via the software application and may be uploaded to the software environment of fluid injection system 104 when connectivity to communication network 112 is not available. In some non-limiting embodiments, the feature may provide an indication of size and/or an indication of status of completion (e.g., a status completion bar) of a software upload to and/or a software download from fluid injection system 104.

In some non-limiting embodiments, a feature associated with determining a location of fluid injection system 104 may provide for transmitting a request for a location of fluid injection system 104, receiving data associated with a location of fluid injection system 104, and determining the location of fluid injection system 104 based on data associated with a location of fluid injection system 104. In some non-limiting embodiments, the request for the location of fluid injection system 104 may include a message (e.g., an RFID based message) that is transmitted via a communication method, such as broadcasting, multicasting, unicasting, and/or the like.

In some non-limiting embodiments, the login process may include a user logging into a computer system, a website, an account, a software platform, a network (e.g., a local network), an intranet, or the like. For example, a user may log into access management system 102 via the mobile application on user device 110. In some non-limiting embodiments, access management system 102 may receive a login request from user device 110 via a mobile application (e.g., a mobile application associated with access management system 102 stored on user device 110). In some non-limiting embodiments, access management system 102 may receive data associated with user identification and may authenticate the user based on the data associated with user identification as part of the login process. For example, the login request may include data associated with user identification and access management system 102 may use all or a portion of the data associated with user identification to authenticate the user. In some non-limiting embodiments, access management system 102 may use a multi-factor authentication process to authenticate a user. For example, access management system 102 may use the data associated with user identification and additional data received from user device 110 during a login process to authenticate the user.

In some non-limiting embodiments, access management system 102 may authenticate the user based on a user license associated with fluid injection system 104. For example, access management system 102 may use the data associated with user identification to determine whether the user is associated with a valid user license. In some non-limiting embodiments, access management system 102 may authenticate the user based on determining that the user is associated with a valid user license. In some non-limiting embodiments, access management system 102 may not authenticate the user based on determining that the user is not associated with a valid user license. In some non-limiting embodiments, access management system 102 may remove access to fluid injection system 104 for a user based on expiration of a user license associated with the user. In some non-limiting embodiments, access management system 102 may authenticate the user for access to specific fluid injection systems (e.g., a specific model of fluid injection system, a fluid injection system with a specific identifier, etc.) based on a user license.

In some non-limiting embodiments, access management system 102 may authenticate the user based on data associated with an identifier of fluid injection system 104. For example, access management system 102 may obtain data associated with an identifier of fluid injection system 104 and use the data associated with user identification and the data associated with an identifier of fluid injection system 104 to determine whether the user is associated with a valid user license for fluid injection system 104. In some non-limiting embodiments, access management system 102 may authenticate the user based on determining that the user is associated with a valid user license for fluid injection system

104 that is identified by the identifier. In some non-limiting embodiments, access management system 102 may not authenticate the user based on determining that the user is not associated with a valid user license for fluid injection system 104 that is identified by the identifier.

In some non-limiting embodiments, access management system 102 may authenticate a user based on an indicator provided by user device 110. For example, a user may use user device 110 to scan an indicator, such as a code (e.g., a barcode, such as a quick response (QR) code, etc.) associated with fluid injection system 104 and access management system 102 may receive data associated with the indicator from user device 110, such data associated with an identifier of fluid injection system 104, and data associated with user identification of the user. Access management system 102 may authenticate the user based on the data associated with an identifier of fluid injection system 104 and the data associated with user identification of the user. In some non-limiting embodiments, access management system 102 may include one or more aspects of a QR code system, and/or other devices and systems, as disclosed in International Patent Application Serial No. PCT/US2021/032659, filed on May 17, 2021, the disclosure of which is incorporated herein by reference in its entirety.

In some non-limiting embodiments, access management system 102 may authenticate the user without connectivity to communication network 112. For example, access management system 102 may authenticate the user via the software application stored on user device 110 when a communication connection to communication network 112 is not available. In some non-limiting embodiments, access management system 102 may determine that connectivity to communication network 112 is not available to user device 110 via the software application and access management system 102 may authenticate the user when connectivity to communication network 112 is available. For example, access management system 102 may determine that connectivity to communication network 112 is not available and access management system 102 may attempt to establish a communication connection to communication network 112 periodically. Access management system 102 may authenticate the user when access management system 102 determines that connectivity to communication network 112 is available via the software application.

In some non-limiting embodiments, access management system 102 may receive the login request and perform an operation based on the login request. For example, access management system 102 may determine whether the data associated with user identification, provided as part of the login request, matches existing data associated with user identification stored in a data structure (e.g., stored in a user profile in a data structure). Access management system 102 may provide a response to user device 110 indicating that the user has successfully logged in or that the data associated with user identification provided as part of the login request does not match existing data associated with user identification stored in the data structure.

In some non-limiting embodiments, access management system 102 may create a user profile (e.g., a user profile for an account) based on the data associated with user identification. For example, if a user that is logging in is determined to be a new user, access management system 102 may create a user profile and store the user profile in a data structure. In some non-limiting embodiments, access management system 102 may create a user profile for an application, for a plurality of applications, for an organization's software environment, or the like. In some non-limiting embodiments, access management system 102 may create and/or revise a user profile based on the data associated with user identification received from user device 110 via the mobile application.

In some non-limiting embodiments, access management system 102 may obtain data associated with user identification to determine that the user is authenticated for access to a software application of fluid injection system 104. For example, a user may provide, via user device 110 (e.g., a mobile application stored on user device 110), a device identifier to access management system 102 and access management system 102 may determine the user's identity based on the device identifier. Access management system 102 may determine that the user's identity is associated with the software application and may authenticate the user for access to the software application. In some non-limiting embodiments, access management system 102 may obtain the data associated with user identification as part of or following a login process.

In some non-limiting embodiments, access management system 102 may facilitate communication between user device 110 of a user and fluid injection system 104. For example, access management system 102 may establish short range wireless communication connection (e.g., a Bluetooth communication connection, a near field communication (NFC) communication connection, etc.) between user device 110 and fluid injection system 104. In another example, access management system 102 may establish a wired communication connection between user device 110 and fluid injection system 104 (e.g., using a universal serial bus (US B) port of each of user device 110 and fluid injection system 104). In some non-limiting embodiments, access management system 102 may facilitate communication between user device 110 of a user and fluid injection system 104 via the software application stored on user device 110 when a communication connection to communication network 112 is not available. In some non-limiting embodiments, access management system 102 may provide data associated with fluid injection system 104 via the software application using the communication connection between user device 110 and fluid injection system 104. In some non-limiting embodiments, access management system 102 may be in communication (e.g., in communication via the software application) with a medical imaging system, a fluid injection system service and control system, a hospital information system, a radiology information system, a service management system (e.g., ServiceMax, SAP Mobile, etc.), and/or a web server (e.g., a web server associated with the software application). In some non-limiting embodiments, access management system 102 may be in communication with a gateway device, one or more systems, and/or one or more applications as disclosed in International Patent Application Serial No. PCT/US2021/040800, filed on Jul. 8, 2021, the disclosure of which is incorporated herein by reference in its entirety.

As shown in FIG. 3, at step 304, process 300 includes providing data identifying one or more features of a software application for accessing the fluid injection system. For example, access management system 102 may provide the data identifying the one or more features of the software application for accessing fluid injection system 104 to user device 110. In some non-limiting embodiments, access management system 102 may provide a plurality of feature identifiers (e.g., a list of identifiers of a plurality of features) of the features of the software application for accessing fluid injection system 104, to a user via a graphical user interface (GUI) on user device 110.

In some non-limiting embodiments, the plurality of feature identifiers may be a subset of all feature identifiers of the software application for accessing fluid injection system 104. For example, the plurality of application identifiers may be associated with a subset of features of the software application that the user is authorized to access (e.g., that are available for access to a user) based on a level of access of the user. In some non-limiting embodiments, the level of access may be based on a user profile of the user. For example, the level of access may be based on a job position (e.g., a role of a user within a company, such as a field services engineer, clinical technician, distributor, bio-medical engineer, etc.) specified in a user profile of the user. In some non-limiting embodiments, access management system 102 may determine one or more features of the software application for accessing fluid injection system 104 for which the user is authorized to access and access management system 102 may provide (e.g., only provide) feature identifiers of the one or more features for which the user is authorized to access.

As shown in FIG. 3, at step 306, process 300 includes receiving data identifying a selected feature of the software application for accessing the fluid injection system. For example, access management system 102 may receive data identifying the selected feature of the software application for accessing fluid injection system 104.

In some non-limiting embodiments, access management system 102 may receive data identifying a selected feature of one or more features of the software application for accessing fluid injection system 104, based on a user's input to a GUI provided via user device 110. In some non-limiting embodiments, access management system 102 may receive information associated with a user selection of a GUI element displayed by the GUI on a screen of user device 110. For example, based on user device 110 detecting a user interaction with the GUI, user device 110 may provide an indication of the user selection to access management system 102. The GUI element may correspond to a selected feature of the one or more features, of which identifying data was provided via the GUI on a screen of user device 110.

In some non-limiting embodiments, access management system 102 may receive a request for access to the selected feature based on a selection of the feature from among a plurality of features. For example, access management system 102 may receive the request for access to the selected feature based on the user selecting a GUI element corresponding to the feature in the GUI on user device 110. In some non-limiting embodiments, access management system 102 may provide a prompt to the user via the GUI on user device 110 to provide information for the request for access to the selected feature. For example, the prompt may request the user to provide data associated with the user that was not previously received and is beneficial for determining whether to provide access to the selected feature.

As shown in FIG. 3, at step 308, process 300 includes providing access to the selected feature of the software application for accessing the fluid injection system. For example, access management system 102 may provide access to the selected feature of the software application for accessing fluid injection system 104. In some non-limiting embodiments, access management system 102 may (e.g., only) provide access to a feature of the software application for accessing fluid injection system 104 to user device 110 (e.g., a user of user device 110) based on access management system 102 authenticating the user for access to fluid injection system 104. In some non-limiting embodiments, access management system 102 may provide access to a specific feature (e.g., a feature associated with remote service procedures of fluid injection system 104) of the software application for accessing fluid injection system 104 to user device 110 based on access management system 102 authenticating the user for access to fluid injection system 104.

In some non-limiting embodiments, access management system 102 may provide access to the selected feature of the software application for accessing fluid injection system 104 stored on user device 110 when a communication connection to communication network 112 is not available. For example, access management system 102 may determine that connectivity to communication network 112 is not available and access management system 102 may attempt to establish a communication connection (e.g., a short range wireless communication connection) between user device 110 and fluid injection system 104. Access management system 102 may provide access to the selected feature of the software application via the communication connection between user device 110 and fluid injection system 104. In some non-limiting embodiments, access management system 102 may provide access to the selected feature of the software application when one or more components (e.g., an injector head, a display, a single board computer printed circuit board (PCB), a servo CPU PCB, etc.), of fluid injection system 104 are being serviced (e.g., removed and/or replaced).

In some non-limiting embodiments, access management system 102 may perform an action associated with the selected feature of the software application for accessing fluid injection system 104. For example, access management system 102 may receive and/or provide data associated with the selected feature of the software application for accessing fluid injection system 104. In specific examples, access management system 102 may scan an error code of fluid injection system 104, generate a service history of fluid injection system 104, provide a service history of fluid injection system 104, provide a list of assets, add an asset to a list of assets, provide a list of features of a software environment of fluid injection system 104 that are covered by a user license, initiate a billing procedure for one or more features of a software environment of fluid injection system 104 that are covered by a user license, add one or more features of a software environment of fluid injection system 104 to a user license, generate a service request for fluid injection system 104, register a warranty, provide data associated with consumables used during fluid injection procedures of fluid injection system 104, provide a list of one or more fluid injection protocols to fluid injection system 104, add or restore one or more fluid injection protocols to fluid injection system 104, provide and/or receive data regarding user preferences of the software application, provide software to a software environment of fluid injection system 104, provide instructions for operation of fluid injection system 104, provide data associated with a service procedure to be performed on fluid injection system 104, and/or provide a complaint regarding a product, such as fluid injection system 104.

In some non-limiting embodiments, access management system 102 may perform an action based on completing the action associated with the selected feature of the software application. For example, access management system 102 may provide the GUI on a display screen of fluid injection system 104 or workstation device 106 that displays an image (e.g., an image of a QR code) and user device 110 may scan the image. User device 110 may determine data associated with the selected feature of the software application, such as a report with regard to a service procedure performed on fluid injection system 104, based on scanning the image. User device 110 may provide the data associated with the selected feature of the software application to access management system 102 via the software application. Access management system 102 may cause fluid injection system 104 to perform a start-up operation (e.g., a restart operation) based on receiving the data associated with the selected feature of the software application. In some non-limiting embodiments, access management system 102 may provide the GUI on the display screen of fluid injection system 104 or workstation device 106 that displays a second image (e.g., a second image of a QR code), and user device 110 may scan the image and generate a secure key via the software application for providing to fluid injection system 104 to cause fluid injection system 104 to perform the start-up operation.

Figure 4A:
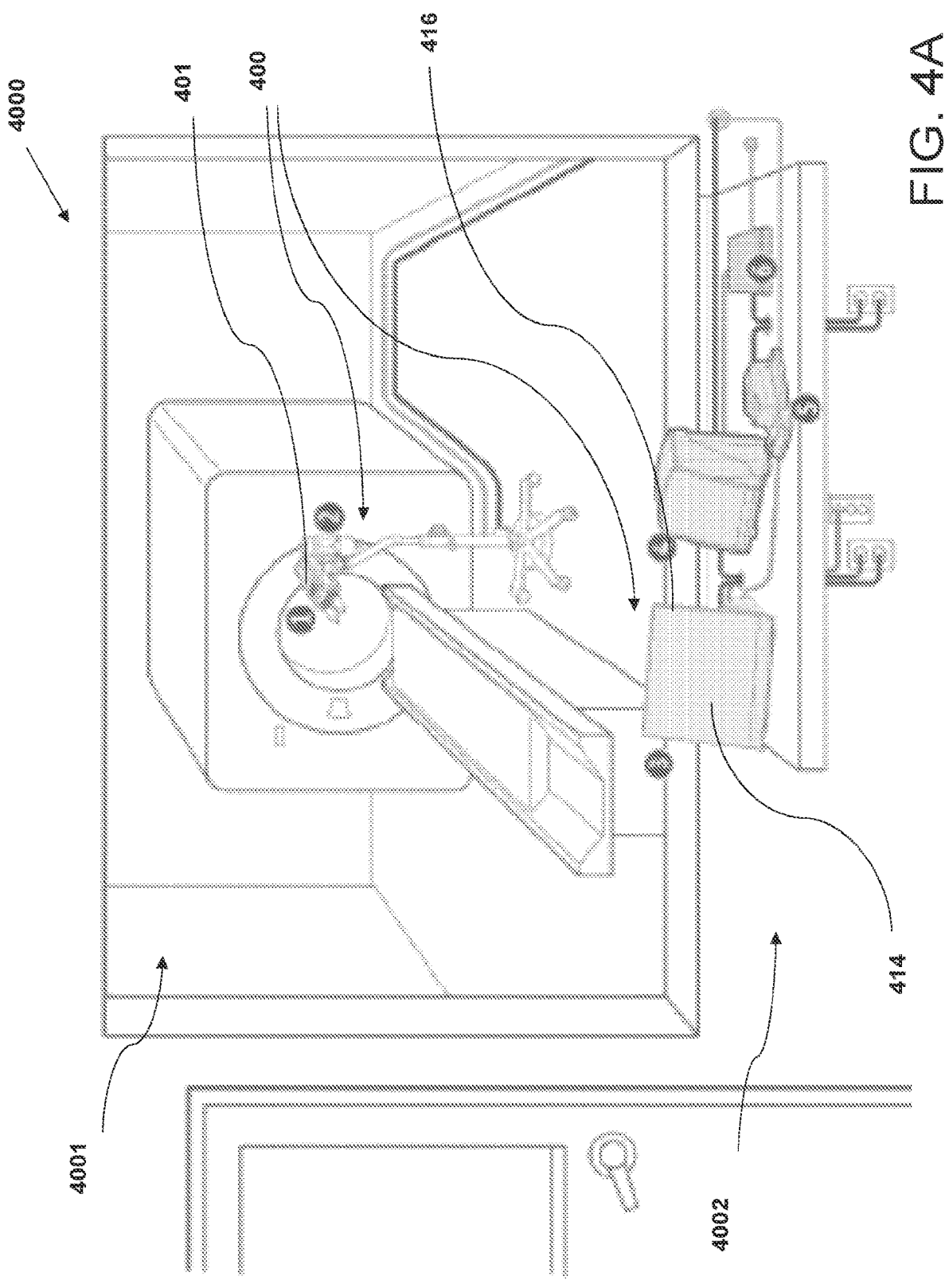
FIG. 4A illustrates a non-limiting example of an imaging suite and a non-limiting embodiment of a fluid injection system therein.
Figure 4B:
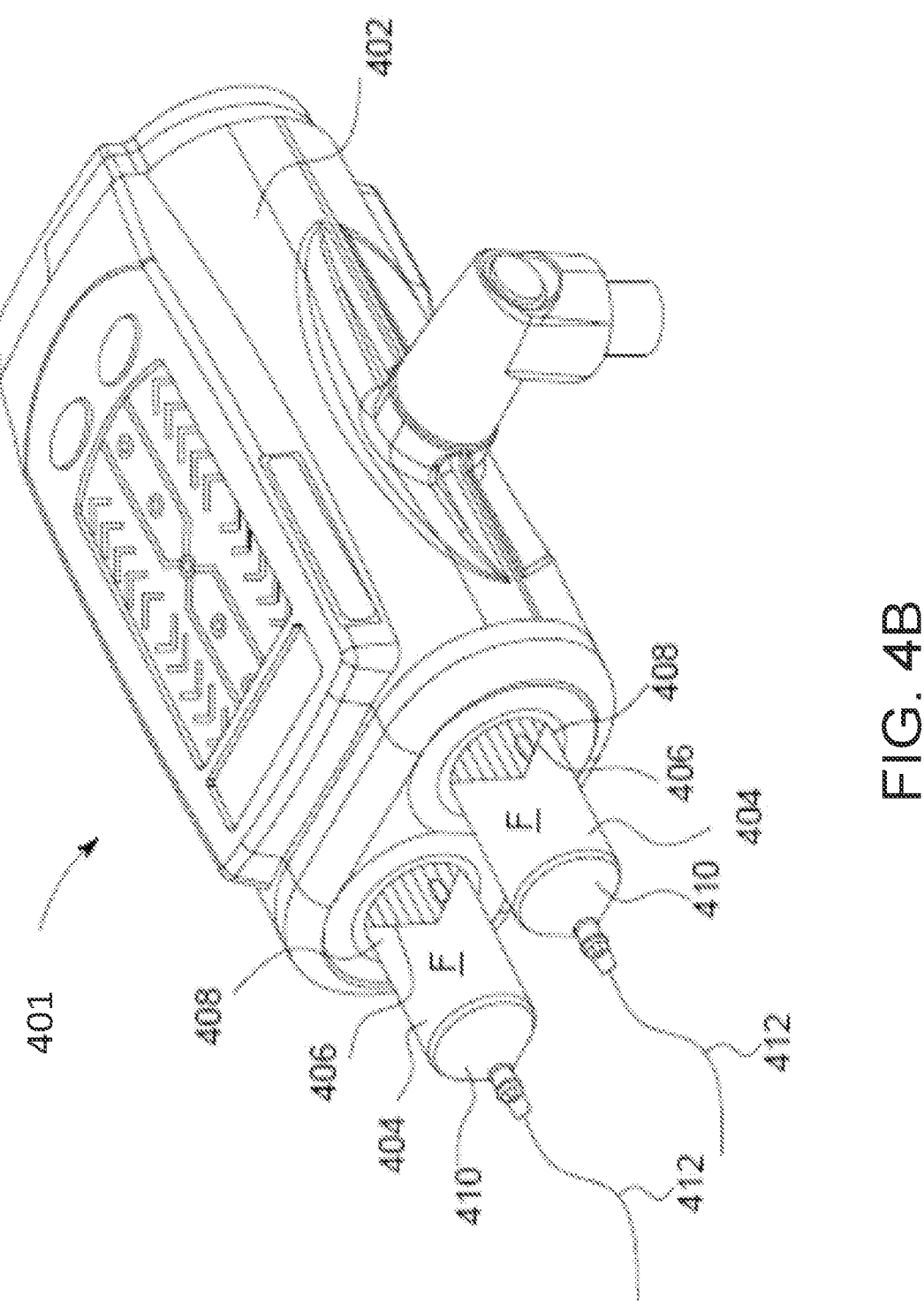
FIG. 4B illustrates an injector head unit of the fluid injection system depicted in FIG. 4A.

Referring now to FIGS. 4A and 4B, FIG. 4A illustrates a non-limiting embodiment of fluid injection system 400, such as the MEDRAD® Stellant FLEX CT Injection System, located in a CT suite 4000. In some non-limiting embodiments, fluid injection system 400 may be the same or similar to fluid injection system 104. As shown in FIG. 4A, fluid injection system 400 may include a bifurcated system that includes a scan room unit and a control room unit thereof located in scan room 4001 and control room 4002, respectively, of CT suite 4000. In non-limiting embodiments, the scan room unit may include injector head unit 401 and the control room unit may include workstation 414, such as the Certegra® Workstation, with display screen 416. As shown in FIG. 4B, injector head unit 401 may include housing 402 and at least one fluid reservoir 404, such as a syringe or a fluid pump container. In some non-limiting embodiments, fluid injection system 400 may include, as best shown in FIG. 4B, a drive component to control fluid flow into or out of a fluid reservoir, such as a piston associated with each of fluid reservoirs 404 that drives plunger 406 within a barrel of fluid reservoir 404. In some non-limiting embodiments, each of fluid reservoirs 404 is adapted to releasably interface with housing 402 at port 408. Each fluid reservoir 404 of fluid injection system 400 is configured to be filled with at least one medical fluid F, such as an imaging contrast media, saline solution, a combination of both the contrast media and the saline solution in a desired ratio, or any other desired medical fluid. Each fluid reservoir 404 may be filled with a different medical fluid F. In some non-limiting embodiments, fluid injection system 400 may be a multi-syringe injector, as shown, where several fluid reservoirs 404 may be oriented side-by-side or in another spatial relationship and are separately actuated by respective pistons associated with fluid injection system 400.

In some non-limiting embodiments, fluid injection system 400 may be used during a medical procedure to inject the at least one medical fluid F into the vasculature of a patient by driving plungers 406 associated with fluid reservoirs 404 with their respective drive components. Each drive component may move its corresponding plunger 406 toward distal end 410 of fluid reservoir 404 to expel the fluid F from fluid reservoir 404 into and through fluid path set 412 during a priming, purging and/or fluid delivery step. In some non-limiting embodiments, fluid path set 412 may include at least one tube or tube set configured to be in fluid communication with each fluid reservoir 404 to place each fluid reservoir 404 in fluid communication with a flexible administration tube and associated catheter for delivering the fluid F from each fluid reservoir 404 to a patient at a vascular access site.

Figure 4C:
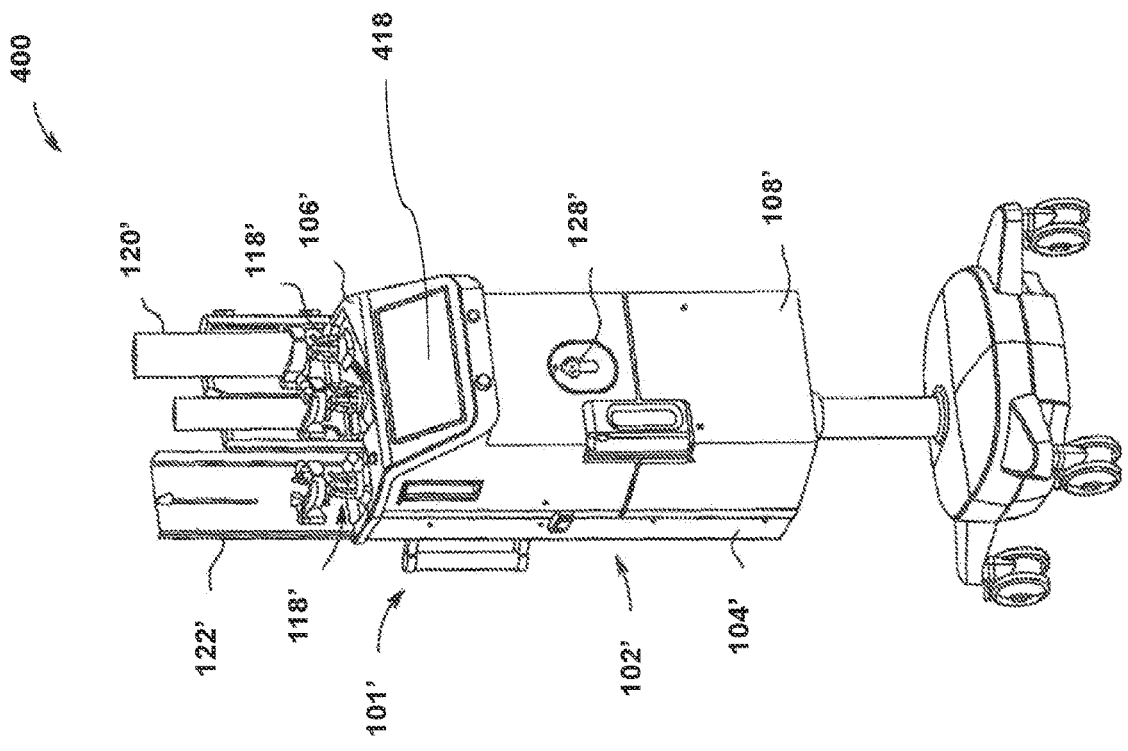
FIG. 4C illustrates another non-limiting embodiment of a fluid injection system.

Referring now to FIG. 4C, FIG. 4C illustrates another non-limiting embodiment of fluid injection system 400, namely a multi-fluid delivery system such as the MEDRAD® Centargo CT Injection System, with display screen 418. As shown in FIG. 4C, fluid injection system 400 may be configured to (e.g., adapted to) provide feedback about compliance with usage instructions. In some non-limiting embodiments, fluid injection system 400 includes powered fluid injector 101' connected to a fluid delivery set intended to be associated with an injector device to deliver fluids from one or more single-dose or multi-dose containers and fluid path sets under pressure into a patient. In some non-limiting embodiments, fluid injector 101' includes injector housing 102' with opposed lateral sides 104', distal or upper end 106', and proximal or lower end 108'. Injector housing 102' encloses the various mechanical drive components, electrical and power components necessary to drive the mechanical drive components, and control components, such as electronic memory and electronic control devices (hereinafter electronic control device(s)), used to control operation of reciprocally movable drive members, such as drive members associated with fluid injection system 400. Such drive members may be reciprocally operable via electro-mechanical drive components, such as a ball screw shaft driven by a motor, a voice coil actuator, a rack-and-pinion gear drive, a linear motor, and the like.

In some non-limiting embodiments, fluid injection system 400 may include at least one bulk fluid connector 118' for connection with at least one bulk fluid source 120'. Alternatively, the fluid source could be a single dose vial, rather than a bulk source. In some examples, a plurality of bulk fluid connectors 118' may be provided. In some non-limiting embodiments, three bulk fluid connectors 118' may be provided in a side-by-side or other arrangement. In some non-limiting embodiments, at least one bulk fluid connector 118' may be a spike configured for removably connecting to the at least one bulk fluid source 120', such as a vial, bottle, or a bag. The at least one bulk fluid connector 118' may have a reusable or non-reusable interface with each new bulk fluid source 120'. The at least one bulk fluid connector 118' may be formed on or attached by tubing with the multi-patient disposable set, as described herein. The at least one bulk fluid source 120' may be configured for receiving a medical fluid, such as saline, an imaging contrast solution, or other medical fluid, for delivery to fluid injection system 400. Injector housing 102' may have at least one support member 122' for supporting the at least one bulk fluid source 120' once it is connected to fluid injection system 400. In some non-limiting embodiments, fluid injection system 400 may include connection port 128' to which a single-use patient line (not shown) connects for enabling the medical fluid(s) to be administered to the patient via a catheter according to a desired injection protocol.

Figure 5A:
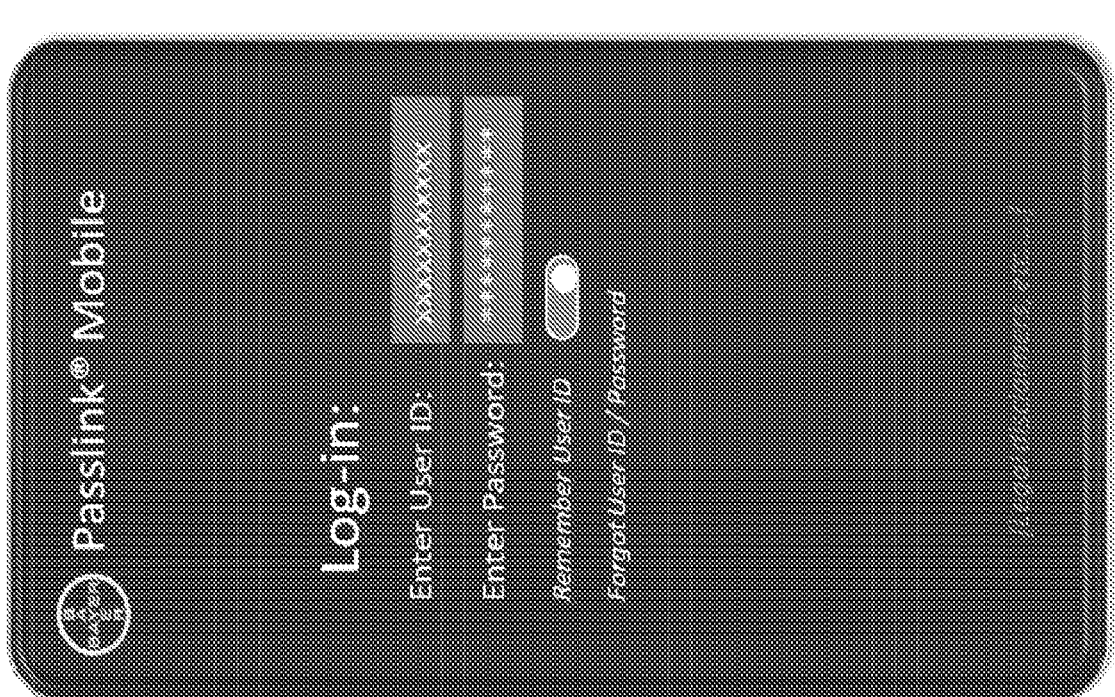
FIGS. 5A-5W are diagrams of non-limiting embodiments of a graphical user interface (GUI) displayed during a process for securely accessing a fluid injection system.
Figure 5B:
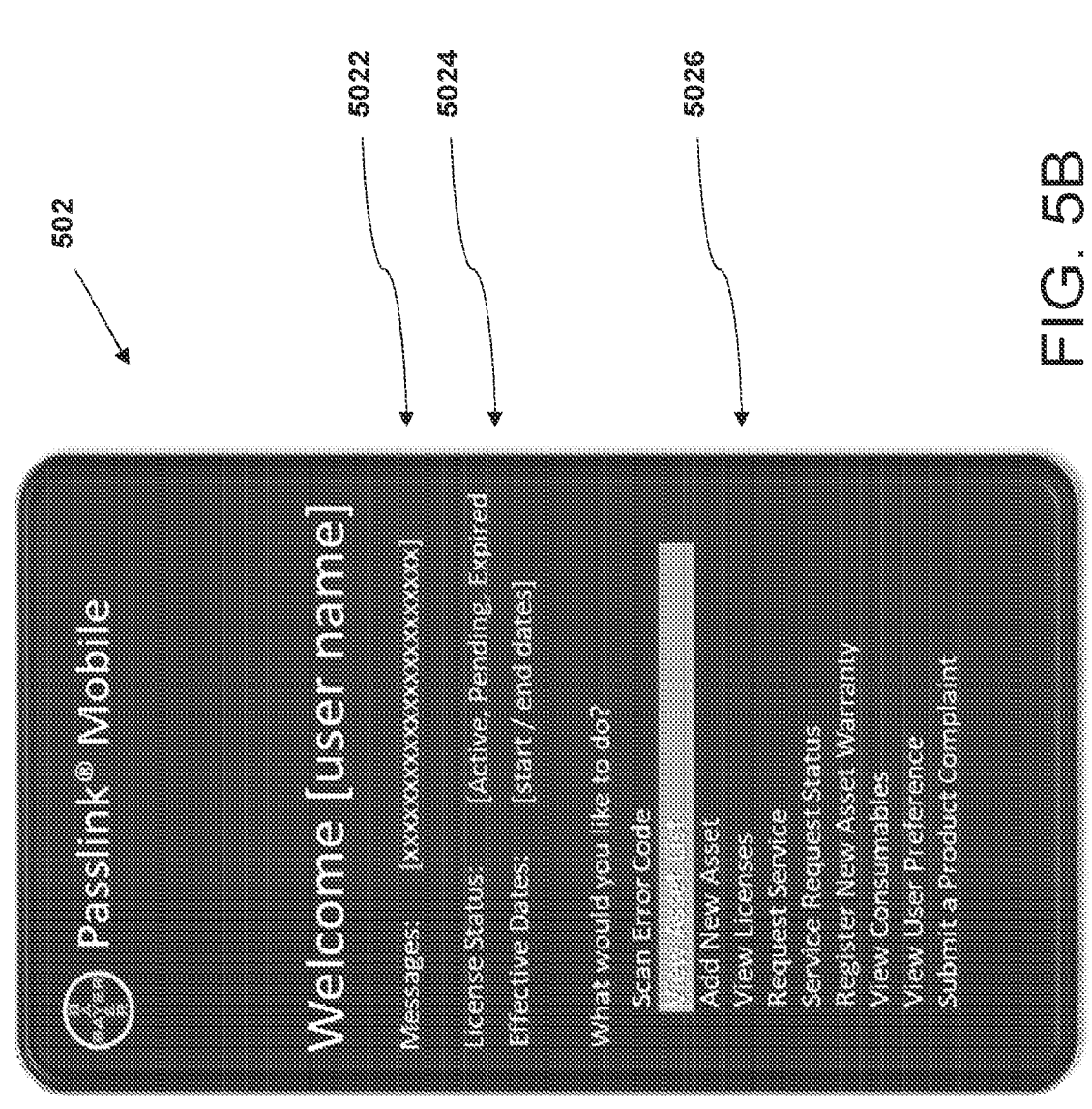
Figure 5C:
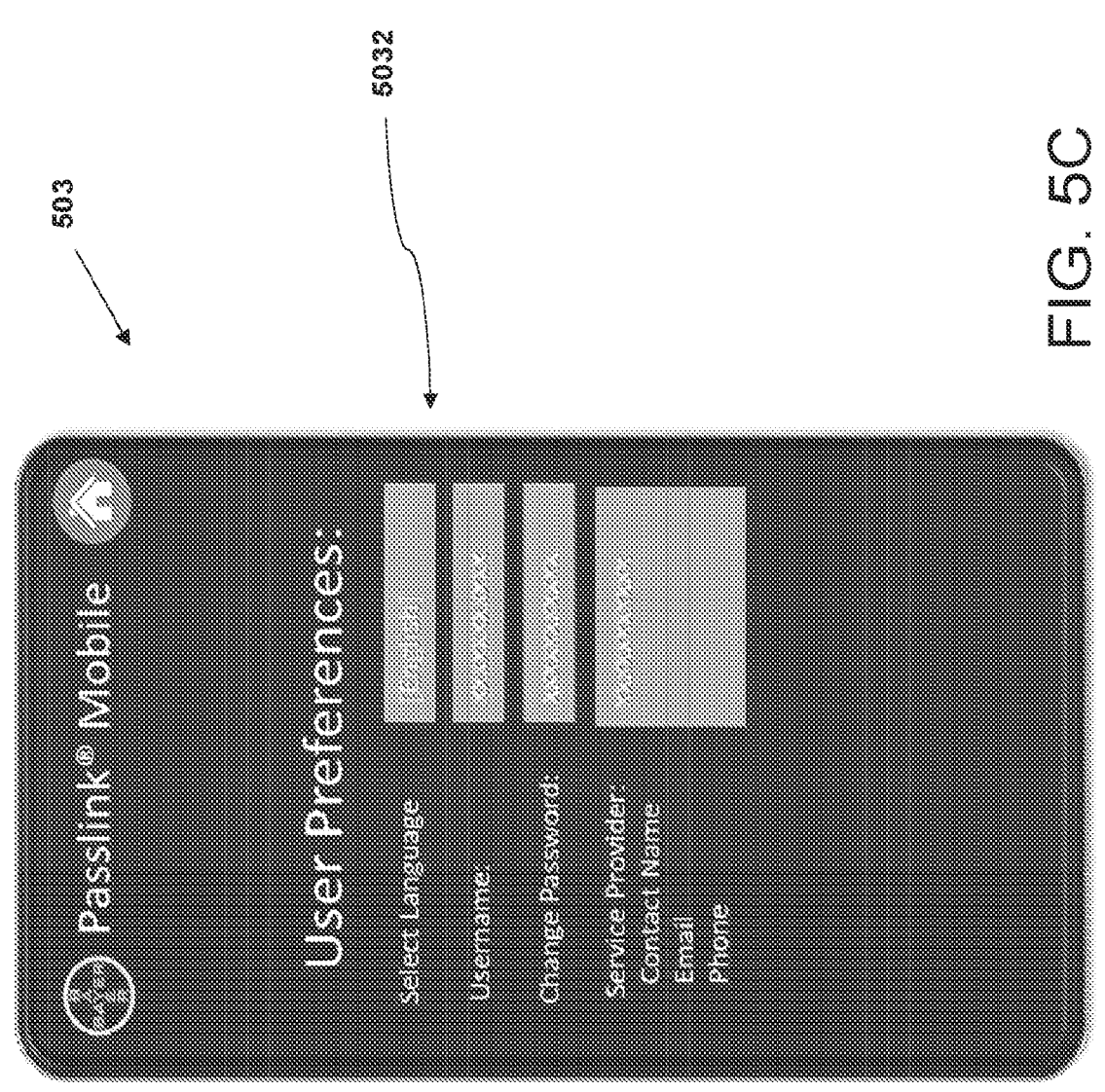
Figure 5D:
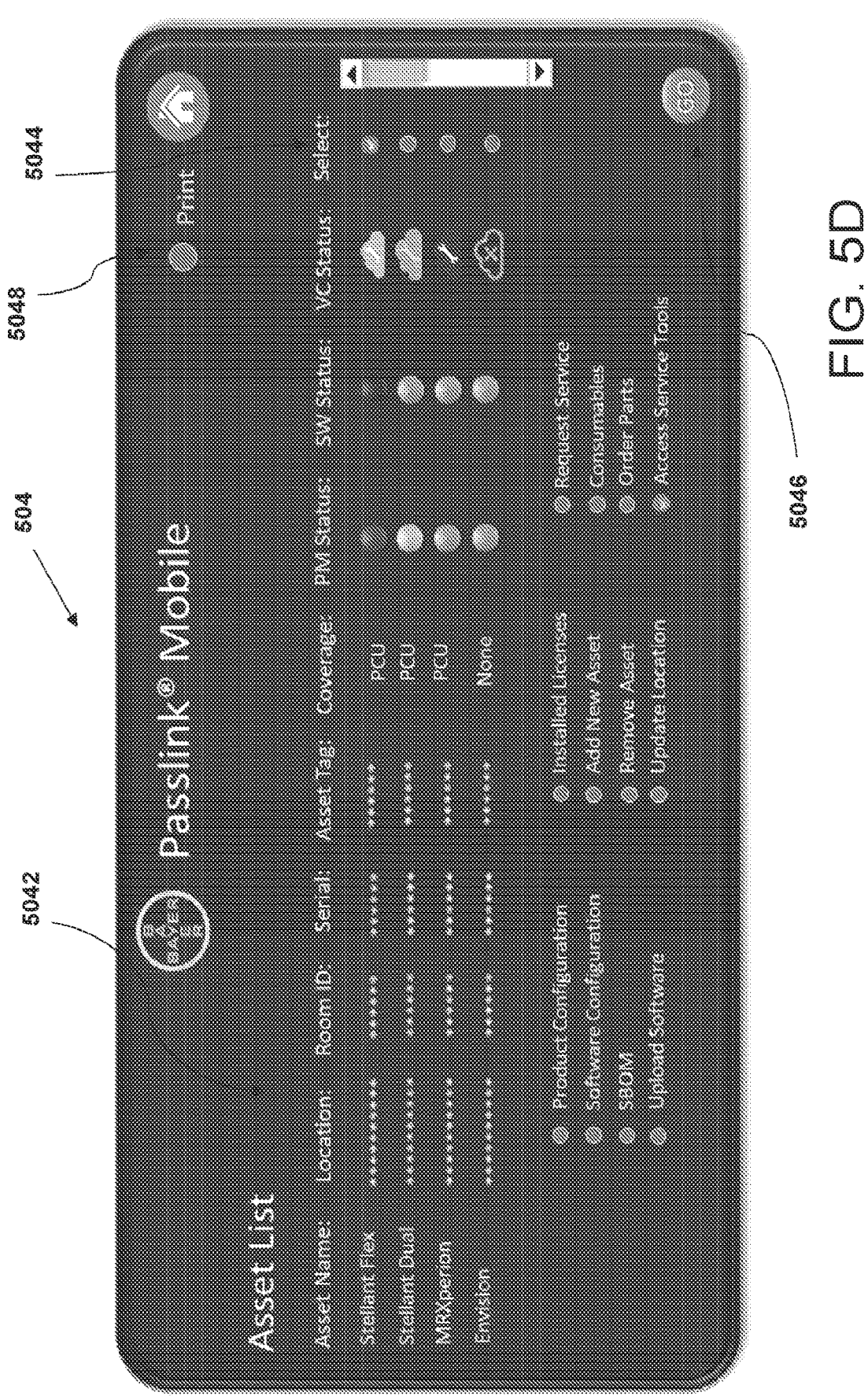
Figure 5E:
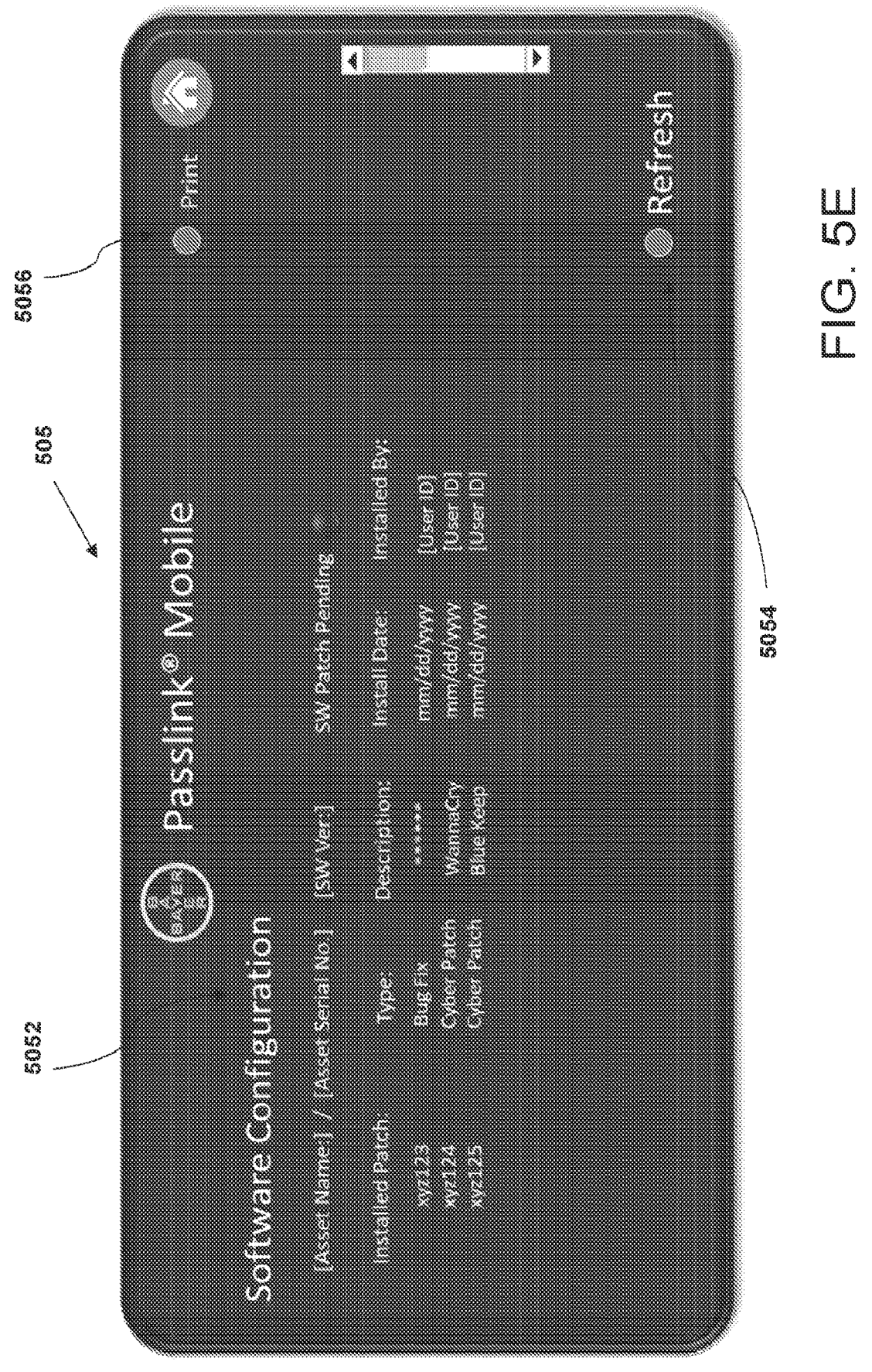
Figure 5F:
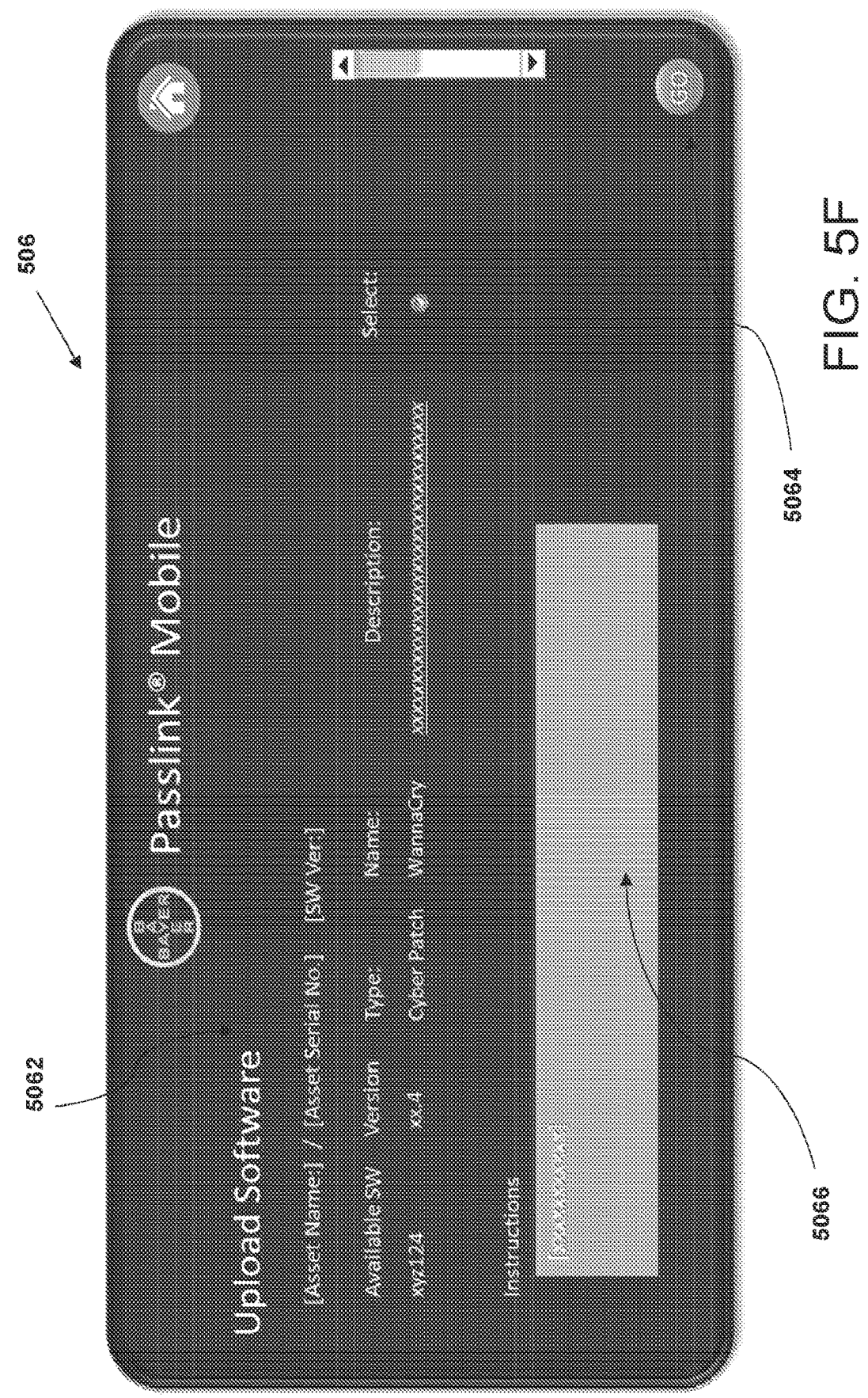
Figure 5G:
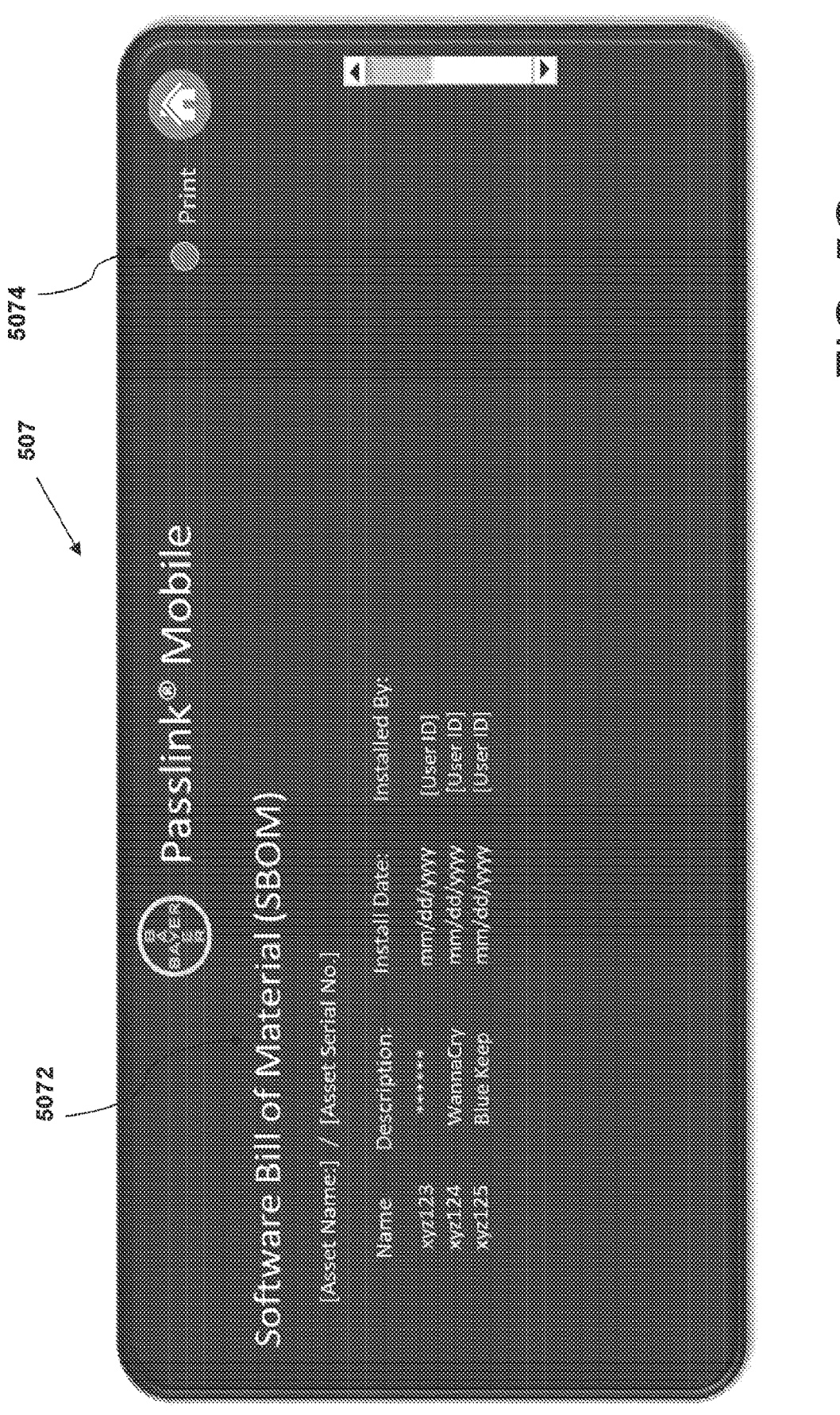
Figure 5H:
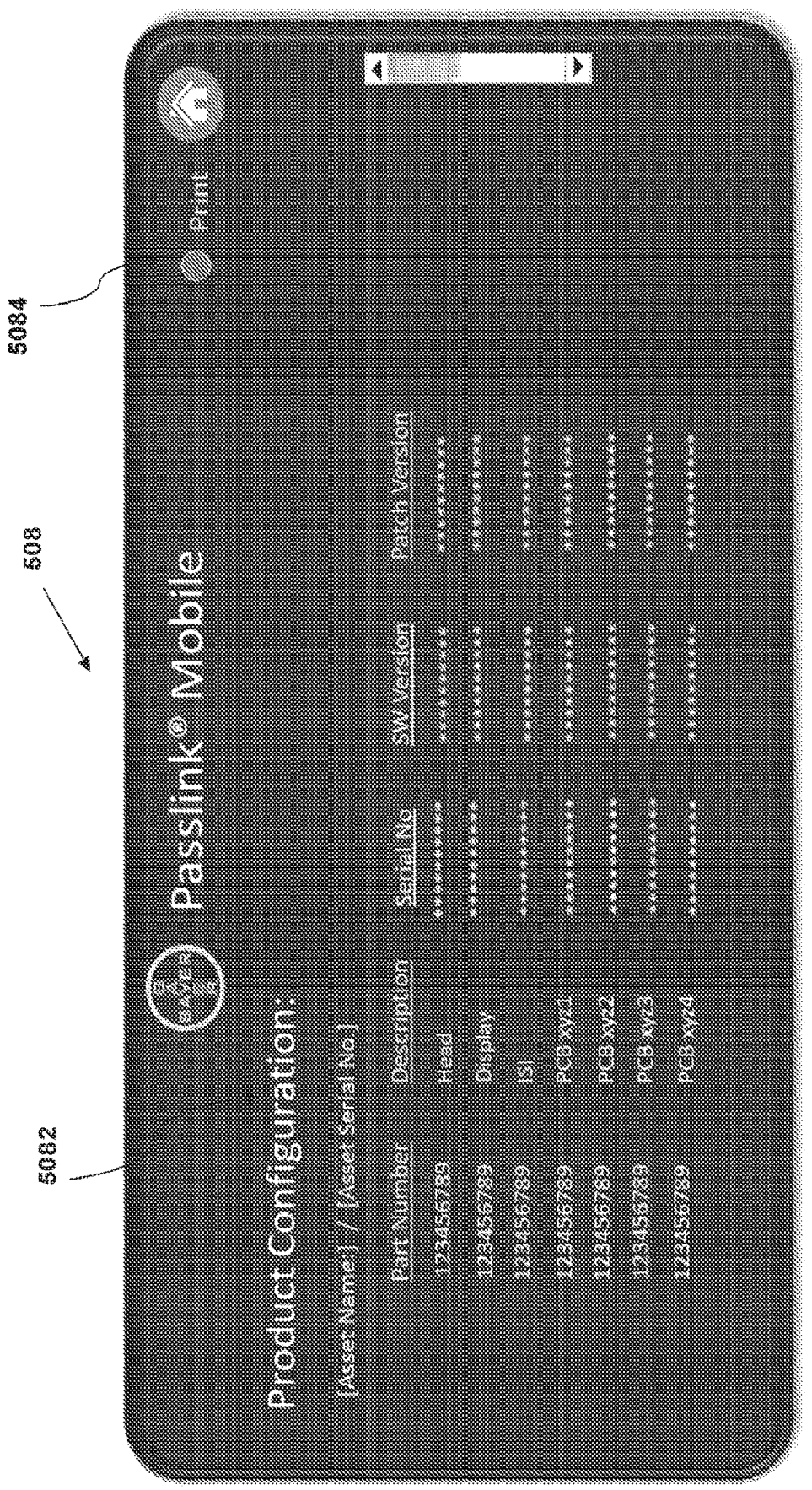
Figure 5I:
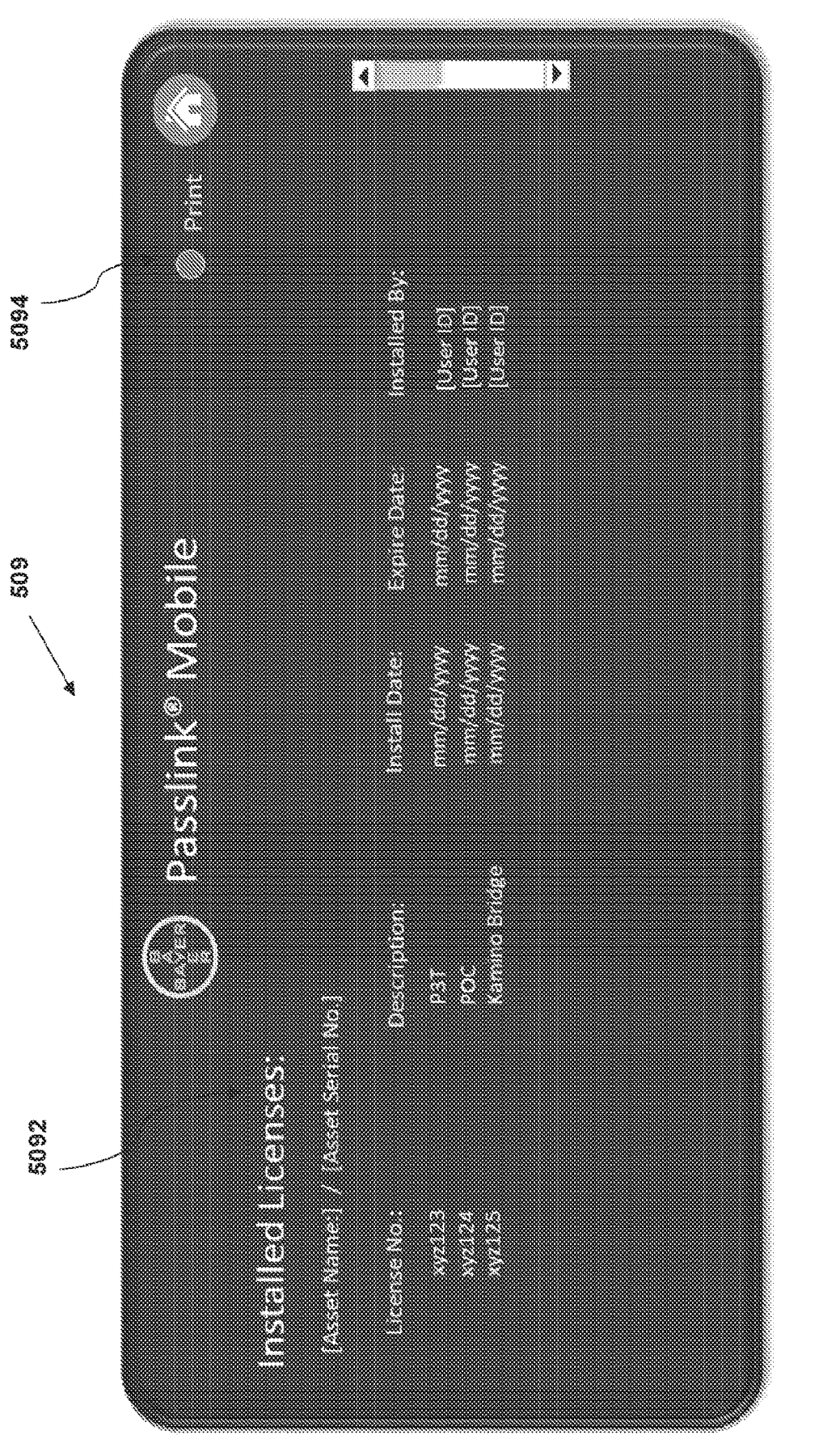
Figure 5J:
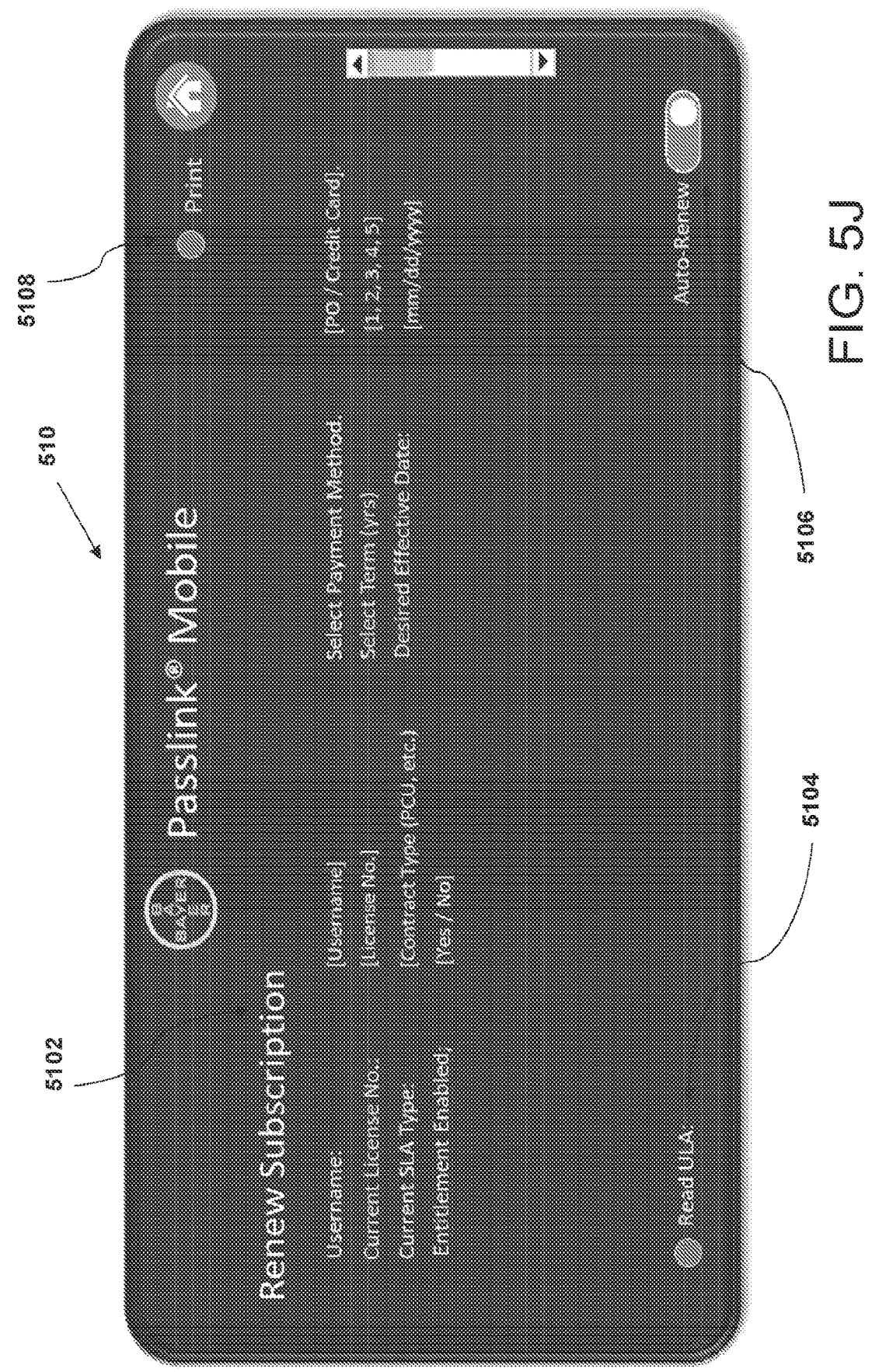
Figure 5K:
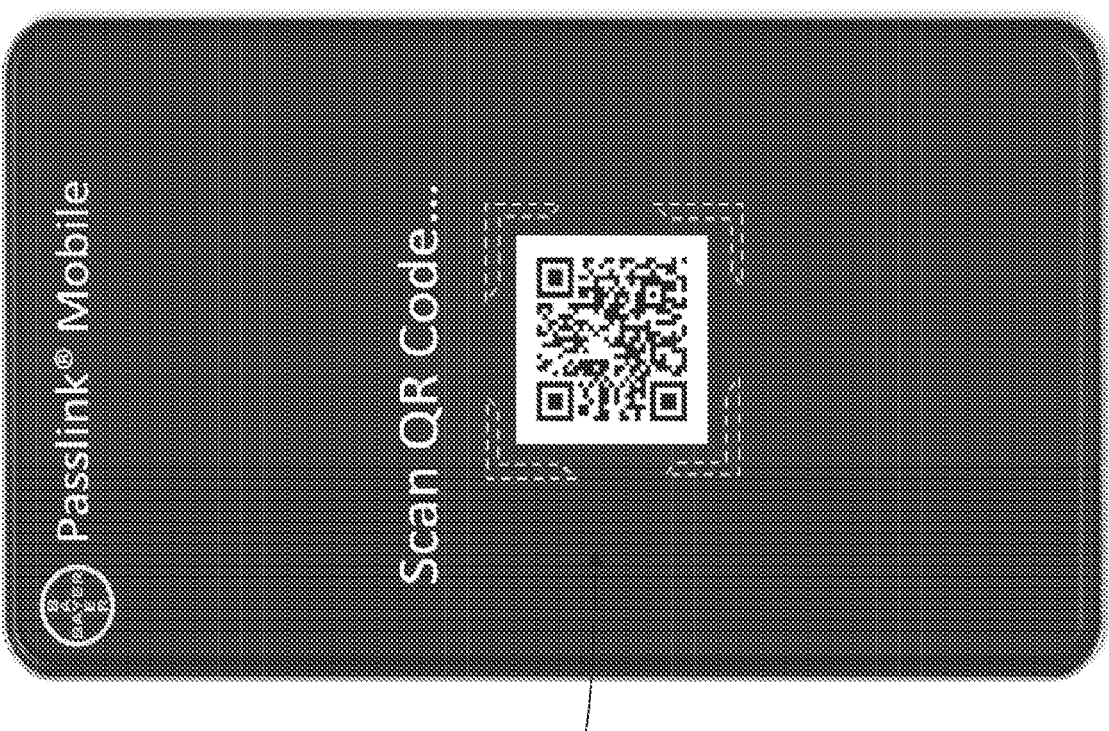
Figure 5L:
Figure 5M:
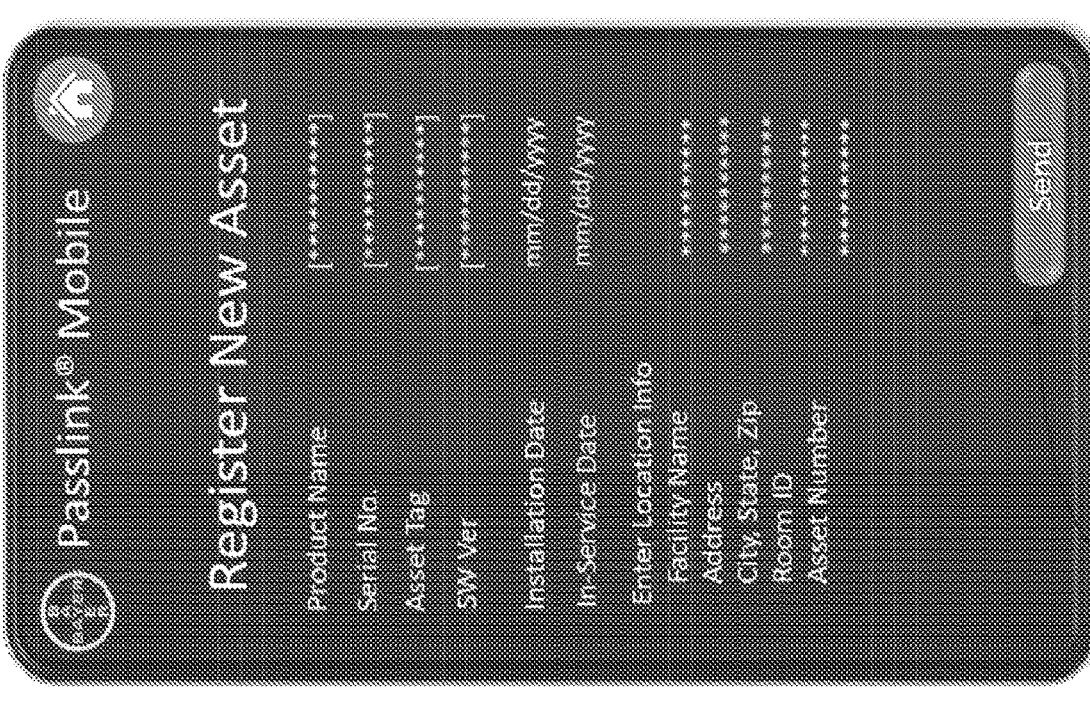
Figure 5N:
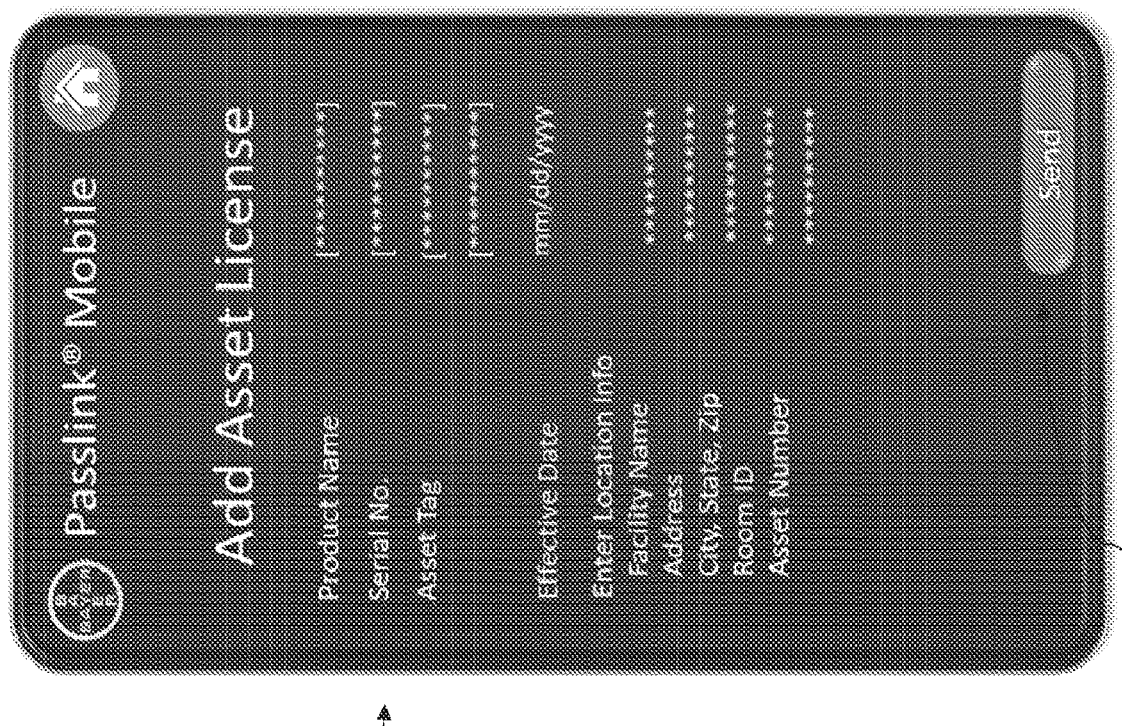
Figure 50:
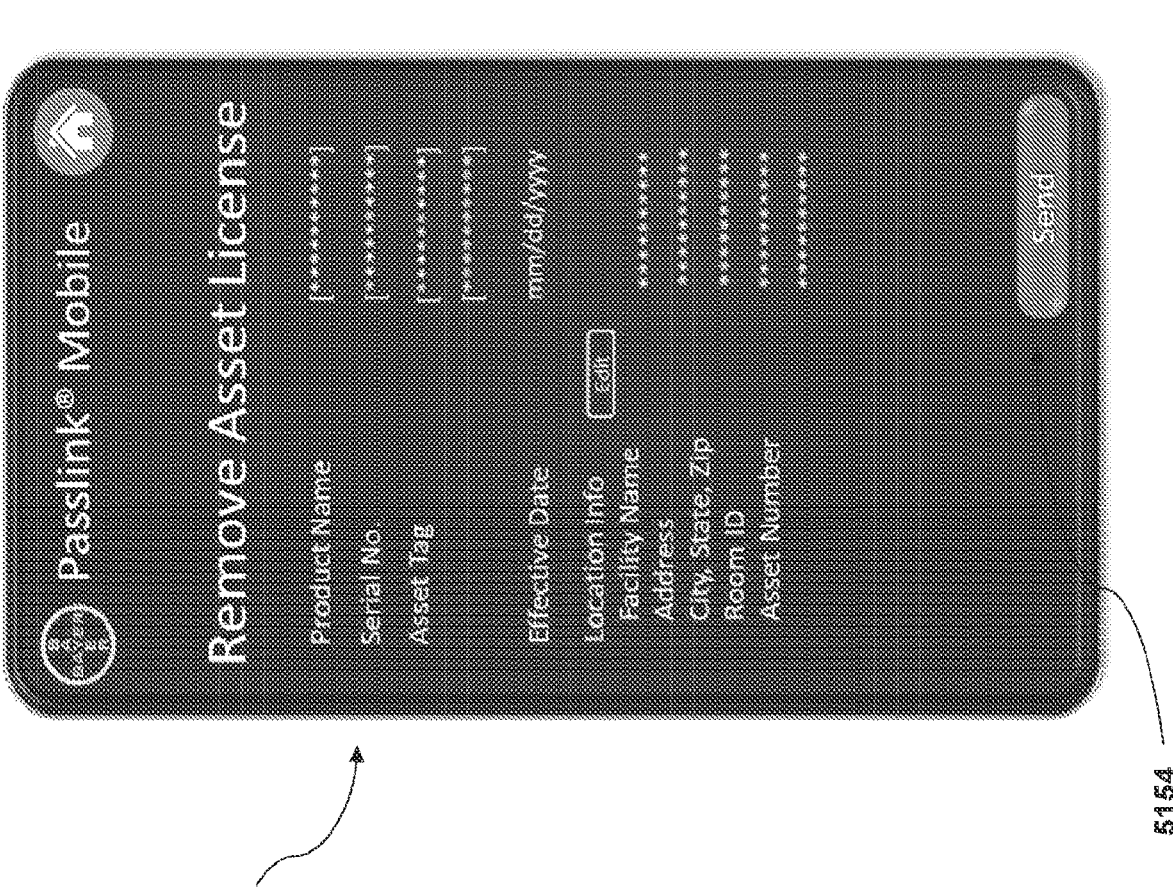
Figure 5P:
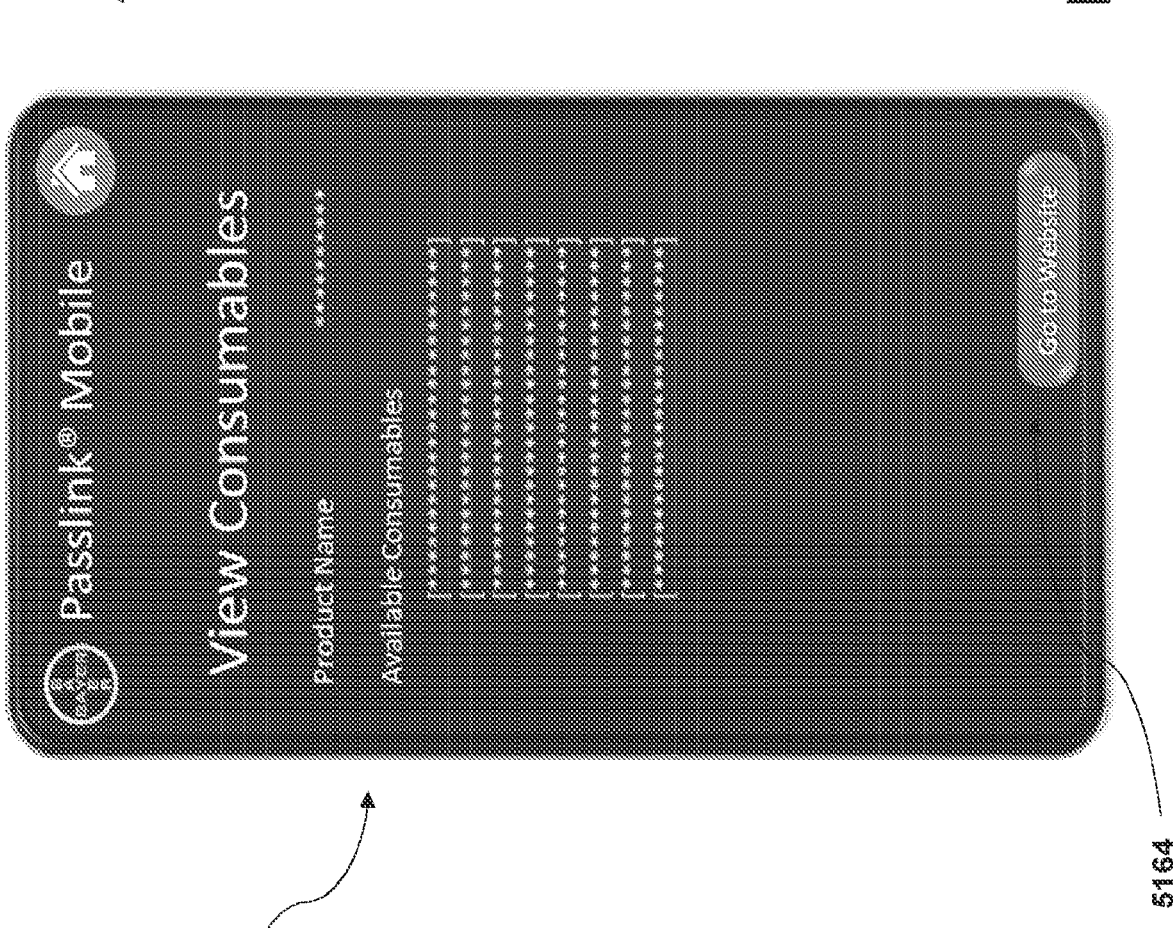
Figure 5Q:
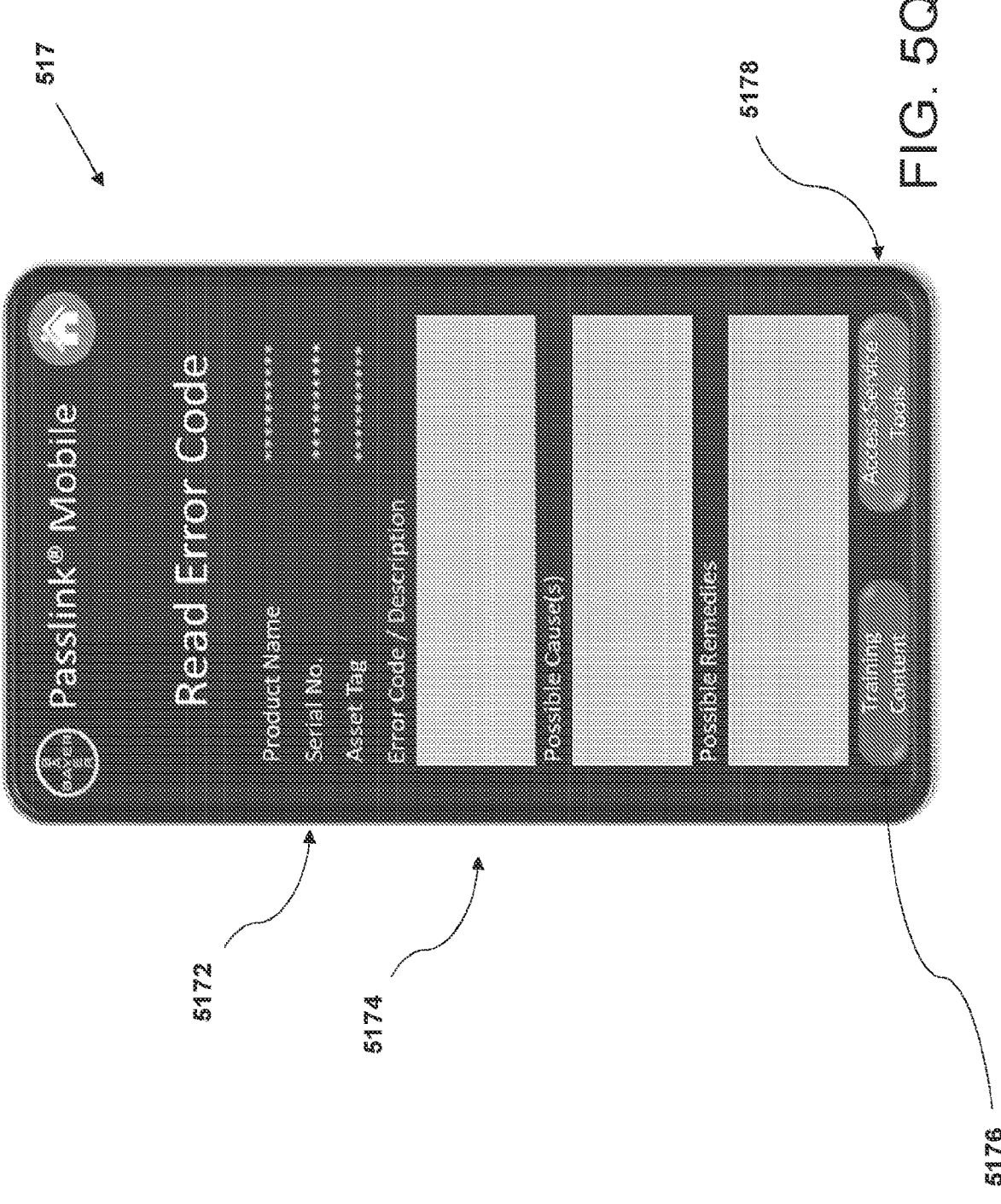
Figure 5S:
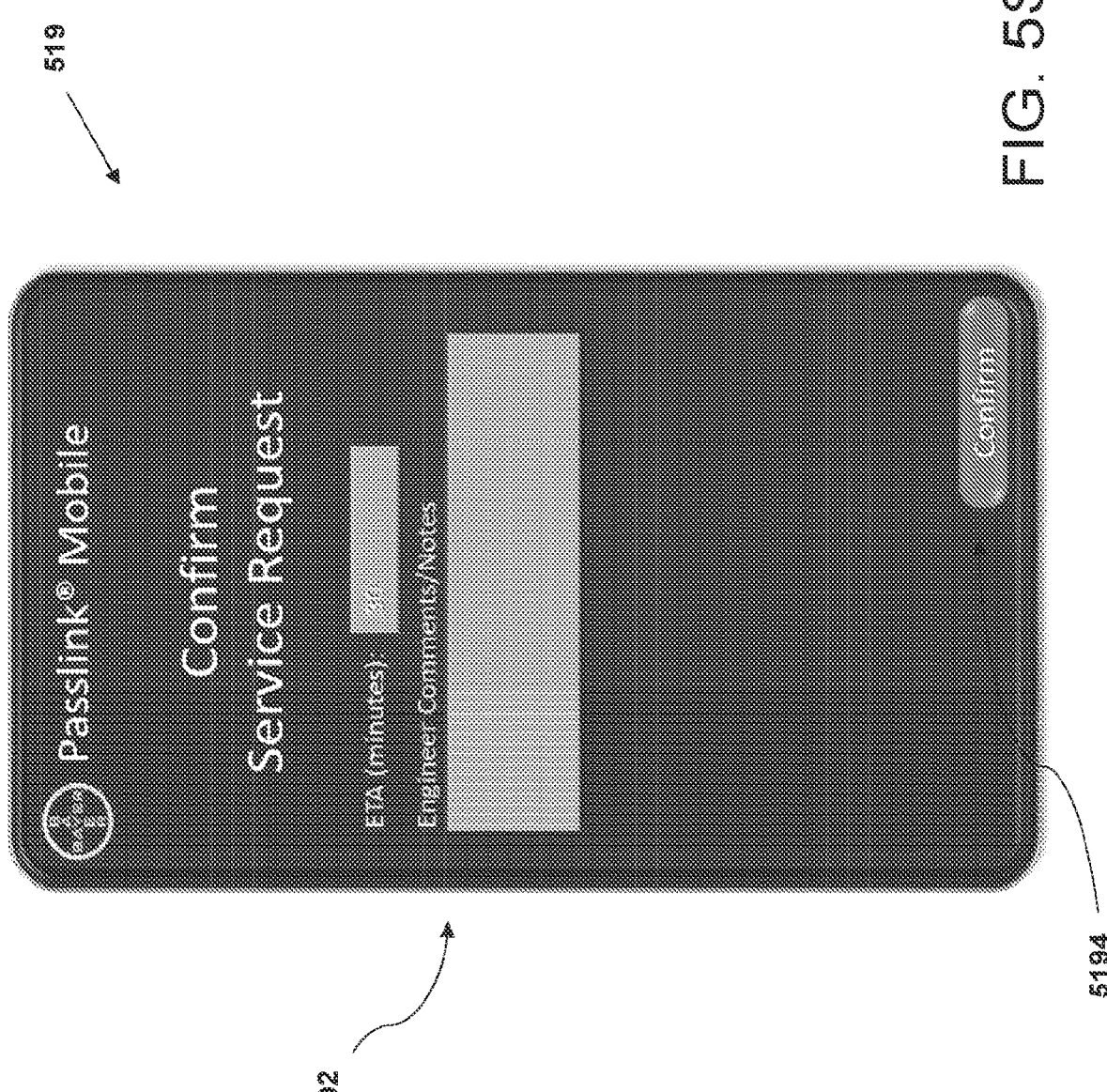
Figure 5T:
Figure 5U:
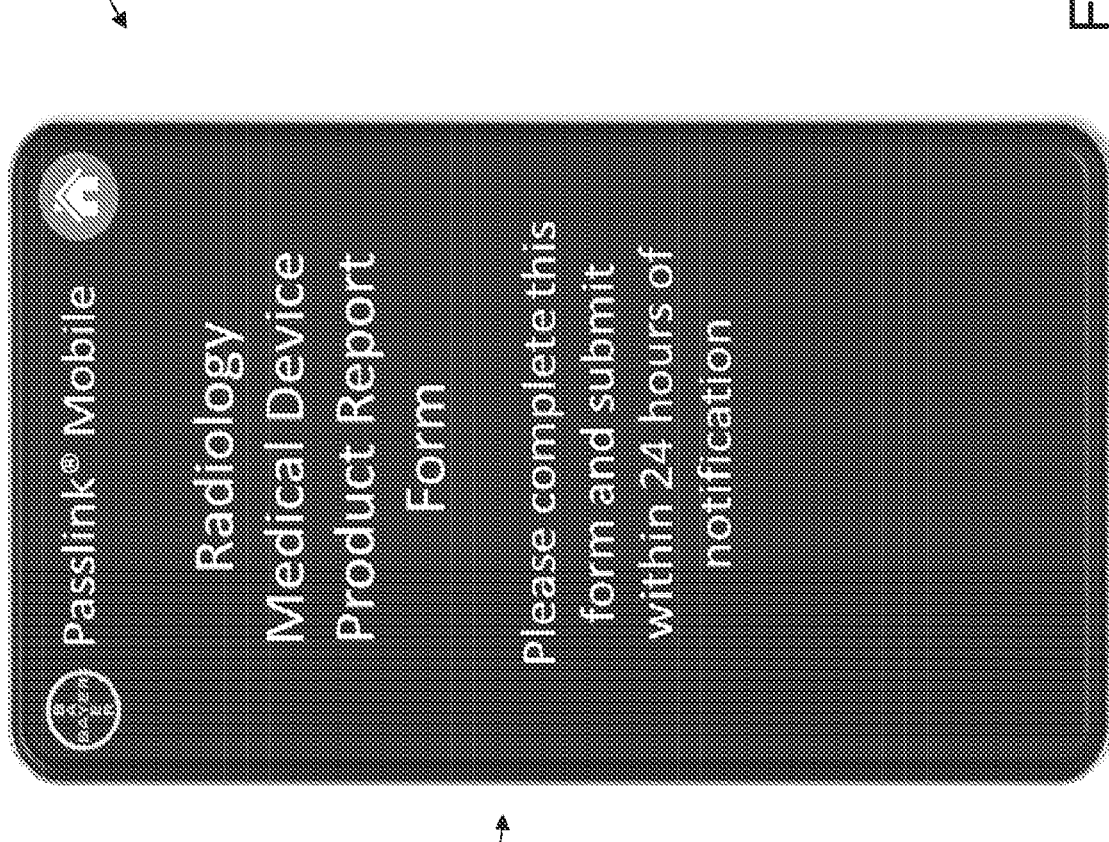
Figure 5V:
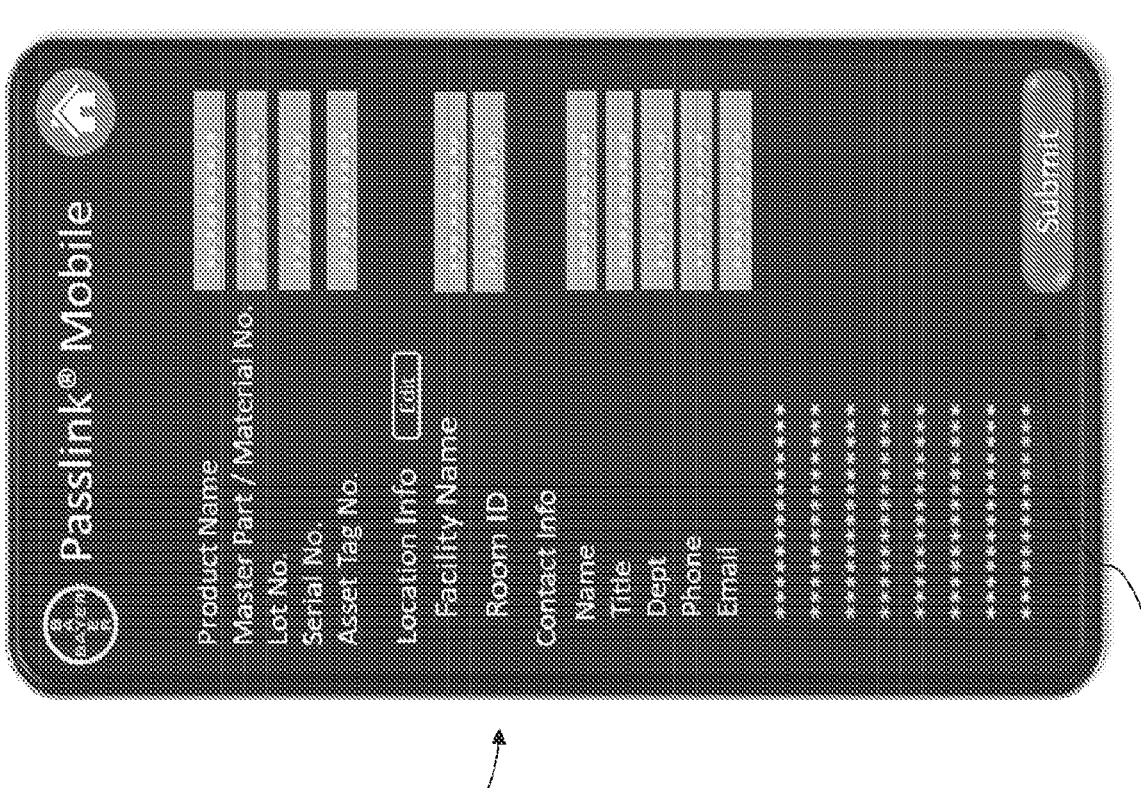
Figure 5W:
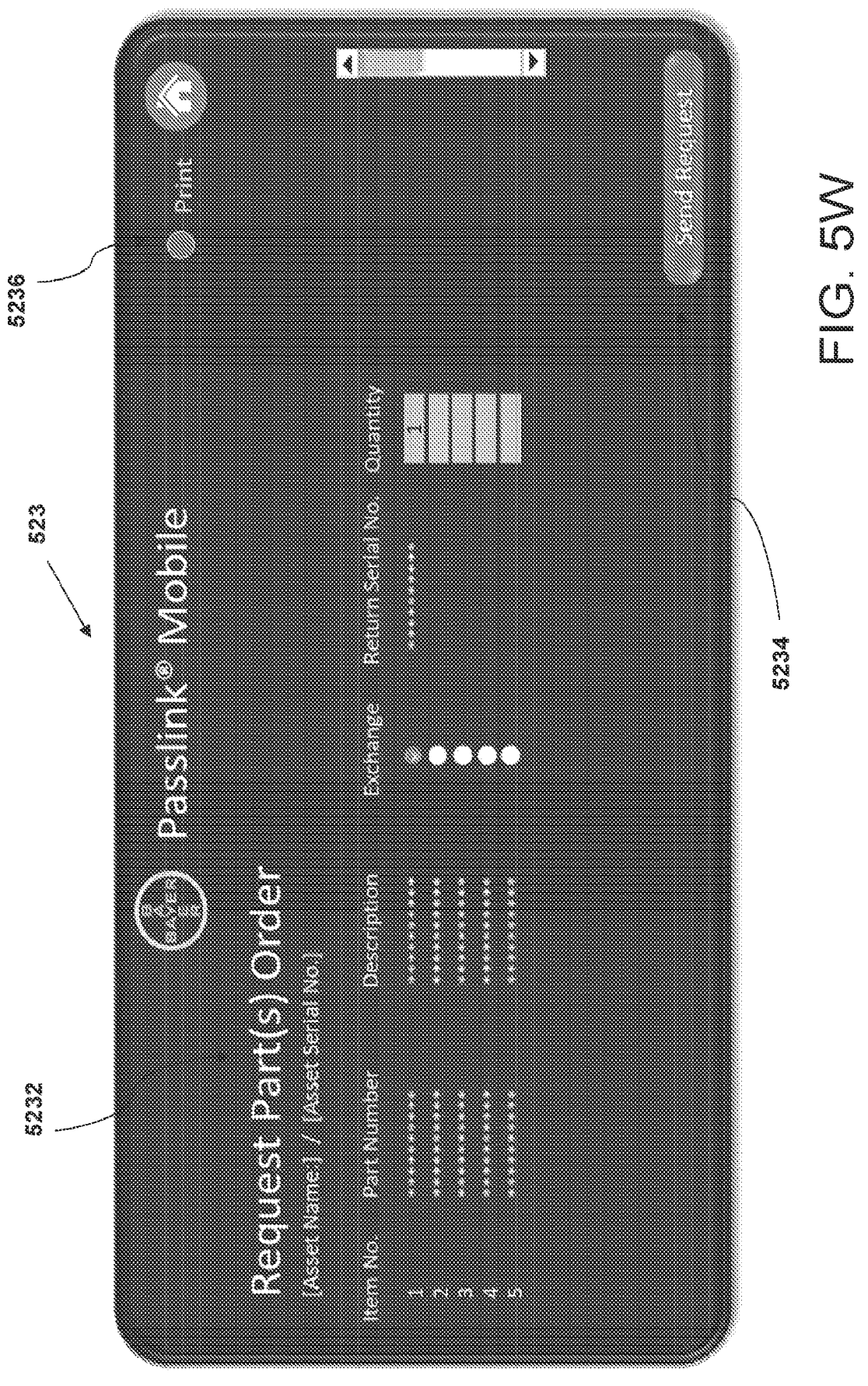

Referring now to FIGS. 5A-5W, FIGS. 5A-5W are diagrams of screens of a GUI that may be provided by access management system 102 via a software application for accessing fluid injection system 104. In some non-limiting embodiments, the screens of the GUI may be provided on a display screen of fluid injection system 104, workstation device 106, user device 110, and/or a separate system or device. In some non-limiting embodiments, an asset as discussed with regard to the description of FIGS. 5A-5W may refer to a fluid injection system, such as fluid injection system 104.

Referring now to FIG. 5A, FIG. 5A is a diagram of GUI 501 that include fields for a user to log into the software application for accessing fluid injection system 104 operated by access management system 102. Referring now to FIG. 5B, FIG. 5B is a diagram of GUI 502 that includes a list of features of the software application for accessing fluid injection system 104. As shown in FIG. 5B, GUI 502 may provide a field 5022 for messages to a user, a field 5024 for data associated with a user license, and a plurality of GUI elements 5026 for selecting a feature of the software application.

Referring now to FIG. 5C, FIG. 5C is a diagram of GUI 503 for a feature associated with providing and/or receiving data regarding user preferences. As shown in FIG. 5C, GUI 503 may provide fields 5032 for inputting user preferences, including a selection of language, a username for a user profile, a password, and data associated with a service provider for service of fluid injection system 104. Referring now to FIG. 5D, FIG. 5D is a diagram of GUI 504 for a feature associated with providing a list of assets. As shown in FIG. 5D, GUI 504 may include field 5042 with data associated with each asset of the list of assets, including an asset name, a location, a room identifier, a serial number, an asset tag number, coverage description, and status descriptions. As further shown in FIG. 5D, GUI 504 may provide GUI element 5044 for selection of an asset and GUI element 5046 for proceeding to another GUI with regard to the selected asset. As further shown in FIG. 5D, GUI 504 may provide GUI element 5048 for printing the data provided in GUI 504.

Referring now to FIG. 5E, FIG. 5E is a diagram of GUI 505 for a feature associated with providing data associated with a software configuration of an asset. As shown in FIG. 5E, GUI 505 may include field 5052 with data associated with a software configuration of an asset, including an asset name, a serial number, a software version, and data associated with software updates. As further shown in FIG. 5D, GUI 504 may provide GUI element 5054 for refreshing the data provided in GUI 505 and GUI element 5056 for printing the data provided in GUI 505. Referring now to FIG. 5F, FIG. 5F is a diagram of GUI 506 for a feature associated with providing software uploads to the software environment of an asset. As shown in FIG. 5F, GUI 506 may include field 5062 with data associated with a software update, including an asset name, a serial number, a software version, and data associated with software updates. As further shown in FIG. 5F, GUI 506 may provide GUI element 5064 for proceeding to another GUI with regard to the selected asset and field 5066 for inputting instructions with regard to the software update.

Referring now to FIG. 5G, FIG. 5G is a diagram of GUI 507 for a feature associated with providing a software bill of materials (SBOM) for an asset. As shown in FIG. 5G, GUI 507 may include field 5072 with data associated with a SBOM, including an asset name, a serial number, and data associated with software updates. As further shown in FIG. 5G, GUI 507 may provide GUI element 5074 for printing data associated with the SBOM provided in GUI 507. Referring now to FIG. 5H, FIG. 5H is a diagram of GUI 508 for a feature associated with providing a product configuration for an asset. As shown in FIG. 5H, GUI 508 may include field 5082 with data associated with a product configuration, including an asset name, a serial number, and data associated with components of an asset (e.g., a part number, a description, a serial number, a software version, and a software update version). As further shown in FIG. 5H, GUI 508 may provide GUI element 5084 for printing data associated with the product configuration provided in GUI 508.

Referring now to FIG. 5I, FIG. 5I is a diagram of GUI 509 for a feature associated with providing data associated with one or more user licenses for an asset. As shown in FIG. 5I, GUI 509 may include field 5092 with data associated with user licenses for an asset, including an asset name, and data associated with the user licenses for an asset (e.g., a license number, a description, an installation date of a license, an expiration date of a license, and an identifier of an installer of a license). As further shown in FIG. 5H, GUI 509 may provide GUI element 5094 for printing data associated with the user licenses for an asset provided in GUI 509.

Referring now to FIG. 5J, FIG. 5J is a diagram of GUI 510 for a feature associated with renewing a subscription associated with a user license for a feature of an asset. As shown in FIG. 5J, GUI 510 may include field 5102 with data associated with renewing a subscription, including a username, a user license number, a service level agreement (SLA), whether entitlement is enabled, a payment method for a subscription, a term for a subscription, and an effective date. As further shown in FIG. 5J, GUI 510 may provide GUI element 5104 for accessing a user license agreement (ULA) and GUI element 5106 for enabling automatic renewal of a subscription. As further shown in FIG. 5J, GUI 510 may provide GUI element 5108 for printing data associated with renewing the subscription provided in GUI 510.

Referring now to FIG. 5K, FIG. 5K is a diagram of GUI 511 for a feature associated with reading a QR code (e.g., a QR code displayed on a display screen). As shown in FIG. 5K, GUI 511 may include a field for capturing (e.g., via an image capture device, such as a camera, of a user device, such as user device 110) an image of a QR code. Referring now to FIG. 5L, FIG. 5L is a diagram of GUI 512 for a feature associated with providing and/or receiving data associated with an asset. As shown in FIG. 5L, GUI 512 may include field 5122 with data associated with an asset, including an asset identifier, a product name, a serial number, an asset tag, a software version, a date of installation, and data associated with a location of an asset (e.g., a facility name, an address of a facility, a room identifier of an asset's location, and an asset number, such as an internal asset number used to identify an asset at a facility). As further shown in FIG. 5L, GUI 512 may provide GUI element 5124 for accessing a list of assets (e.g., via GUI 504).

Referring now to FIG. 5M, FIG. 5M is a diagram of GUI 513 for a feature associated with registering an asset (e.g., registering an asset to a list of assets of a user license, registering an asset to a list of assets of a user profile, etc.). As shown in FIG. 5M, GUI 513 may include field 5132 with data associated with an asset, including an asset identifier, a product name, a serial number, an asset tag, a software version, a date of installation, an in-service date, and data associated with a location of an asset (e.g., a facility name, an address of a facility, a room identifier of an asset's location, and an asset number, such as an internal asset number used to identify an asset at a facility). As further shown in FIG. 5M, GUI 513 may provide GUI element 5134 for transmitting the data associated with an asset provided in GUI 513 for a registration procedure.

Referring now to FIG. 5N, FIG. 5N is a diagram of GUI 514 for a feature associated with adding a user license associated with an asset. As shown in FIG. 5N, GUI 514 may include field 5142 with data associated with an asset, including an asset identifier, a serial number, an asset tag, an effective date of the user license, and data associated with a location of an asset (e.g., a facility name, an address of a facility, a room identifier of an asset's location, and an asset number, such as an internal asset number used to identify an asset at a facility). As further shown in FIG. 5N, GUI 514 may provide GUI element 5144 for transmitting the data associated with an asset provided in GUI 514 to add the user license associated with the asset.

Referring now to FIG. 5O, FIG. 5O is a diagram of GUI 515 for a feature associated with removing a user license associated with an asset. As shown in FIG. 5O, GUI 515 may include field 5152 with data associated with an asset, including an asset identifier, a serial number, an asset tag, an effective date of the user license, and data associated with a location of an asset (e.g., a facility name, an address of a facility, a room identifier of an asset's location, and an asset number, such as an internal asset number used to identify an asset at a facility). As further shown in FIG. 5O, GUI 515 may provide GUI element 5154 for transmitting the data associated with an asset provided in GUI 514 to remove the user license associated with the asset.

Referring now to FIG. 5P, FIG. 5P is a diagram of GUI 516 for a feature associated with providing data associated with consumables used during fluid injection procedures with an asset. As shown in FIG. 5P, GUI 516 may include field 5162 with data associated with a consumable of an asset, including a product name and data associated with available consumables for an asset. As further shown in FIG. 5P, GUI 516 may provide GUI element 5164 for providing a link to website associated with a consumable.

Referring now to FIG. 5Q, FIG. 5Q is a diagram of GUI 517 for a feature associated with associated with reading an error code generated by an asset. As shown in FIG. 5Q, GUI 517 may be displayed following a user device reading a QR code that provides an error code. As further shown in FIG. 5Q, GUI 517 may include field 5172 with data associated with an asset that generated an error code, including a product name, a serial number, and an asset tag. As further shown in FIG. 5Q, GUI 517 may include a plurality of fields 5174 for inputting data associated with an error code, including a description of an error code, a possible cause of an error code, and a possible remedy for an error code. As further shown in FIG. 5Q, GUI 517 may provide GUI element 5176 for providing a link to training content for an asset and GUI element 5178 for accessing a feature of an asset associated with service tools of the asset.

Referring now to FIG. 5R, FIG. 5R is a diagram of GUI 518 for a feature associated with generating a service request for an asset. As shown in FIG. 5R, GUI 518 may include field 5182 with data associated with an asset, including a product name, a serial number, an asset tag, data associated with a location of an asset (e.g., a facility name and a room identifier of an asset's location), data associated with a contact for a service request (e.g., an individual name and phone number), data associated with an error code generated by an asset. As further shown in FIG. 5R, GUI 518 may include a field 5184 for inputting data associated with a symptom of an asset that is a reason for a service request and a severity (e.g., high, medium, or low) of the symptom. As further shown in FIG. 5R, GUI 518 may provide GUI element 5186 for transmitting the service request.

Referring now to FIG. 5S, FIG. 5S is a diagram of GUI 519 for a feature associated with generating a confirmation of receipt of a service request for an asset. As shown in FIG. 5S, GUI 519 may include field 5192 for inputting data associated with a confirmation of a service request (e.g., an estimated time of arrival and comments from an individual that is confirming receipt of the service request). As further shown in FIG. 5S, GUI 519 may provide GUI element 5194 for transmitting the confirmation of receipt of a service request.

Referring now to FIG. 5T, FIG. 5T is a diagram of GUI 520 for a feature associated with providing a status of a service request for an asset. As shown in FIG. 5T, GUI 520 may include field 5202 for inputting data associated with a status of a service request (e.g., an indication that a service request was transmitted, an indication that a confirmation of receipt of a service request was transmitted, an estimated time of arrival, an indication that a service request is complete, data associated with contacting an individual that is confirming receipt of the service request, and a field for inputting data associated with a service request, etc.). As further shown in FIG. 5T, GUI 520 may include field 5204 for inputting comments regarding a status of a service request for an asset.

Referring now to FIG. 5U, FIG. 5U is a diagram of GUI 521 for a feature associated with providing a product report for an asset. As shown in FIG. 5U, GUI 521 may include field 5212 for providing data associated with a notice for a product report. In some non-limiting embodiments, GUI 521 may be generated and provided following completion of a service request.

Referring now to FIG. 5V, FIG. 5V is a diagram of GUI 522 for a feature associated with providing a product report for an asset. As shown in FIG. 5V, GUI 522 may include field 5222 with data associated with an asset, including a product name, a part number (e.g., a master part number, a material number, etc.), a lot number, a serial number, an asset tag number, data associated with a location of an asset (e.g., a facility name and a room identifier of an asset's location), and data associated with a contact for a product report (e.g., an individual's name, title, department, phone number, and email address). As further shown in FIG. 5V, GUI 522 may provide GUI element 5224 for transmitting the product report.

Referring now to FIG. 5W, FIG. 5W is a diagram of GUI 523 for a feature associated with providing a component (e.g., part) request for an asset. As shown in FIG. 5W, GUI 523 may include field 5232 for inputting data associated with a component request for an asset (e.g., an asset identifier, an asset serial number, an item number, a part number, a description, an indication of whether a component is being exchanged, a return serial number, and an indication of a quantity). As further shown in FIG. 5W, GUI 523 may provide GUI element 5234 for transmitting the component request.

Although the present disclosure has been described in detail for the purpose of illustration based on what is currently considered to be the most practical and preferred embodiments, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more aspects of any embodiment can be combined with one or more aspects of any other embodiment.

What is claimed is:

1. A system for accessing a fluid injection system comprising:

at least one processor programmed or configured to:

authenticate a user for access to a fluid injection system, wherein the fluid injection system is configured to administer contrast fluid including a contrast agent to a patient, wherein, when authenticating the user for access to the fluid injection system, the at least one processor is programmed or configured to:

provide a graphical user interface (GUI) on a display screen that displays an image to scan by a user device associated with the user, receive a login credential associated with the image via a software application for accessing the fluid injection system, the software application being on the user device associated with the user, and authenticate the user for access to the fluid injection system based on receiving the login credential via the software application;

provide data identifying one or more features of the software application for accessing the fluid injection system based on an input received via the software application, wherein the one or more features of the software application comprises:

one or more features associated with providing data associated with the fluid injection system, wherein the one or more features associated with providing data associated with the fluid injection system comprises:

a feature associated with obtaining data associated with an error code of the fluid injection system, a feature associated with generating a service history of the fluid injection system, a feature associated with providing the service history of the fluid injection system, a feature associated with generating a service request for the fluid injection system, a feature associated with providing instructions for operation of the fluid injection system, a feature associated with providing data associated with a service procedure to be performed on the fluid injection system, a feature associated with providing data associated with a service procedure that was performed on the fluid injection system, or any combination thereof;

receive data identifying a selected feature of the software application for accessing the fluid injection system;

determine whether the user is authorized to access the selected feature of the software application based on authenticating the user for access to the fluid injection system, wherein, when determining whether the user is authorized to access selected feature of the software application, the at least one processor is programmed or configured to:

determine whether the user has a level of access that authorizes the user to access the selected feature of the software application, wherein the level of access is based on a user profile of the user; and provide access to the selected feature of the software application for accessing the fluid injection system based on determining that the user is authorized to access the selected feature of the software application.

2. The system of claim 1, wherein the at least one processor is further programmed or configured to:

display the data associated with the selected feature of the software application for accessing the fluid injection system via a graphical user interface (GUI) of the software application on the user device.

3. The system of claim 1, wherein the fluid injection system comprises a display screen, and wherein the at least one processor is further programmed or configured to:

cause data associated with the fluid injection system to be displayed on the display screen of the fluid injection system.

4. The system of claim 1, wherein the at least one processor is further programmed or configured to:

access the selected feature of the software application of the fluid injection system to provide data associated with the fluid injection system, wherein the data associated with the fluid injection system comprises data associated with one or more operations of the fluid injection system; and wherein the at least one processor is further programmed or configured to:

log the data associated with one or more operations of the fluid injection system.

5. A computer program product for accessing a fluid injection system, the computer program product comprising at least one non-transitory computer-readable medium including one or more instructions that, when executed by at least one processor, cause the at least one processor to:

authenticate a user for access to a fluid injection system, wherein the fluid injection system is configured to administer contrast fluid including a contrast agent to a patient, wherein, the one or more instructions that cause the at least one processor to authenticate the user for access to the fluid injection system, cause the at least one processor to:

provide a graphical user interface (GUI) on a display screen associated with the fluid injection system that displays an image to scan by a user device, receive a login credential associated with the image via a software application for accessing the fluid injection system, and authenticate the user for access to the fluid injection system based on receiving the login credential via the software application;

provide data identifying one or more features of the software application for accessing the fluid injection system based on an input received via the software application, wherein the one or more features of the software application comprises:

one or more features associated with providing data associated with the fluid injection system, wherein the one or more features associated with providing data associated with the fluid injection system comprises:

a feature associated with obtaining data associated with an error code of the fluid injection system, a feature associated with generating a service history of the fluid injection system, a feature associated with providing the service history of the fluid injection system, a feature associated with generating a service request for the fluid injection system, a feature associated with providing instructions for operation of the fluid injection system, a feature associated with providing data associated with a service procedure to be performed on the fluid injection system, a feature associated with providing data associated with a service procedure that was performed on the fluid injection system, or any combination thereof;

receive data identifying a selected feature of the software application of the fluid injection system;

determine whether the user is authorized to access the selected feature of the software application based on authenticating the user for access to the fluid injection system, wherein, the one or more instructions that cause the at least one processor to determine whether the user is authorized to access selected feature of the software application, cause the at least one processor to:

determine whether the user has a level of access that authorizes the user to access the selected feature of the software application, wherein the level of access is based on a user profile of the user; and provide access to the selected feature of the software application of the fluid injection system based on determining that the user is authorized to access the selected feature of the software application.

6. The computer program product of claim 5, wherein the one or more instructions further cause the at least one processor to:

display data associated with the selected feature of the software application of the fluid injection system via a graphical user interface (GUI) of the software application on the user device.

7. The computer program product of claim 5, wherein the fluid injection system comprises a display screen, and wherein the one or more instructions further cause the at least one processor to:

cause data associated with the fluid injection system to be displayed on the display screen of the fluid injection system.

8. The computer program product of claim 5, wherein the one or more instructions further cause the at least one processor to:

access the selected feature of the software application for accessing the fluid injection system to provide data associated with the fluid injection system, wherein the data associated with the fluid injection system comprises data associated with one or more operations of the fluid injection system; and wherein the one or more instructions further cause the at least one processor to:

log the data associated with the one or more operations of the fluid injection system.

9. A method for accessing a fluid injection system comprising:

authenticating, with at least one processor, a user for access to a fluid injection system, wherein the fluid injection system is configured to administer contrast fluid including a contrast agent to a patient, wherein, when authenticating the user for access to the fluid injection system, the at least one processor is programmed or configured to;

providing a graphical user interface (GUI) on a display screen associated with the fluid injection system that displays an image to scan by a user device associated with the user, receiving a login credential associated with the image via a software application for accessing the fluid injection system, the software application being on the user device associated with the user, and authenticating the user for access to fluid injection system based on receiving the login credential via the software application;

providing, with the at least one processor, data identifying one or more features of the software application for accessing the fluid injection system based on an input received via the software application, wherein the one or more features of the software application comprises:

one or more features associated with providing data associated with the fluid injection system, wherein the one or more features associated with providing data associated with the fluid injection system comprises:

a feature associated with obtaining data associated with an error code of the fluid injection system, a feature associated with generating a service history of the fluid injection system, a feature associated with providing the service history of the fluid injection system, a feature associated with generating the service request for the fluid injection system, a feature associated with providing instructions for operation of the fluid injection system, a feature associated with providing data associated with a service procedure to be performed on the fluid injection system, a feature associated with providing data associated with a service procedure that was performed on the fluid injection system, or any combination thereof;

receiving, with the at least one processor, data identifying a selected feature of the software application for accessing the fluid injection system;

determining, with the at least one processor, whether the user is authorized to access the selected feature of the software application based on authenticating the user for access to the fluid injection system, wherein determining whether the user is authorized to access selected feature of the software application comprises:

determining whether the user has a level of access that authorizes the user to access the selected feature of the software application, wherein the level of access is based on a user profile of the user; and providing, with the at least one processor, access to the selected feature of the software application for accessing the fluid injection system based on determining that the user is authorized to access the selected feature of the software application.

10. The method of claim 9, further comprising:

displaying data associated with the selected feature of the software application of the fluid injection system via a graphical user interface (GUI) of the software application on the user device.

11. The method of claim 9, wherein the fluid injection system comprises the display screen, and wherein the method further comprises:

causing data associated with the fluid injection system to be displayed on the display screen of the fluid injection system.

12. The method of claim 9, further comprising:

accessing the selected feature of the software application for accessing the fluid injection system to provide data associated with the fluid injection system, wherein the data associated with the fluid injection system comprises data associated with one or more operations of the fluid injection system; and wherein the method further comprises:

logging the data associated with the one or more operations of the fluid injection system.

* * * * *